(12) United States Patent
Olomutzki et al.

(10) Patent No.: US 9,301,773 B2
(45) Date of Patent: Apr. 5, 2016

(54) LEAD EXTRACTION METHODS AND APPARATUS

(75) Inventors: Yoav Olomutzki, Kfar Saba (IL); Roey Shafrir, Modi'in (IL); Jacob Koren, Haifa (IL)

(73) Assignee: Leadex Cardiac Ltd., Herzliya (IL)

( * ) Notice: Subject to any disclaimer, the term of this patent is extended or adjusted under 35 U.S.C. 154(b) by 673 days.

(21) Appl. No.: 12/686,572

(22) Filed: Jan. 13, 2010

(65) Prior Publication Data

US 2010/0198229 A1    Aug. 5, 2010

Related U.S. Application Data

(60) Provisional application No. 61/144,176, filed on Jan. 13, 2009.

(51) Int. Cl.
| A61B 19/00 | (2006.01) |
| A61B 17/3205 | (2006.01) |
| A61B 17/00 | (2006.01) |
| A61N 1/05 | (2006.01) |
| A61B 17/34 | (2006.01) |

(52) U.S. Cl.
CPC ....... *A61B 17/32053* (2013.01); *A61B 17/3468* (2013.01); *A61B 2017/00539* (2013.01); *A61B 2017/00544* (2013.01); *A61N 1/056* (2013.01)

(58) Field of Classification Search
CPC .................. A61B 17/3468; A61N 2001/0578; F16L 55/26–55/48
USPC ......... 606/108, 129, 130, 159, 167, 171, 180, 606/184; 607/119, 122, 126, 127, 128; 604/95.01, 95.04; 600/114, 115, 116
See application file for complete search history.

(56) References Cited

U.S. PATENT DOCUMENTS

| 3,763,864 | A |   | 10/1973 | Dremann |
| 4,176,662 | A | * | 12/1979 | Frazer ........................... 600/114 |
| 4,576,162 | A |   | 3/1986  | McCorkle |
| 4,848,168 | A | * | 7/1989  | Negishi ........................ 73/865.8 |
| 5,013,310 | A | * | 5/1991  | Goode et al. ...................... 606/1 |
| 5,398,670 | A | * | 3/1995  | Ortiz et al. .................... 600/114 |

(Continued)

FOREIGN PATENT DOCUMENTS

| JP | 63-255168 A | 10/1988 |
| JP | 2008-155033 A | 10/2008 |

OTHER PUBLICATIONS

International Search Report and Written Opinion from International Patent Application No. PCT/IB2010/000206 mailed Apr. 8, 2010.

(Continued)

*Primary Examiner* — Katherine Rodjom
*Assistant Examiner* — Jonathan Hollm
(74) *Attorney, Agent, or Firm* — Wolf, Greenfield & Sacks, P.C.

(57) ABSTRACT

According to one aspect, a device for assisting in removing an implanted lead is provided. The device comprises a body portion having a center adapted to accommodate the lead, a cutting component coupled to the body portion to assist in separating tissue from the lead, and at least one anchoring component disposed at least partially within the body portion, the at least one anchoring component capable of providing pressure on the lead that resists movement of at least part of the body portion along the lead at least in part by applying fluid pressure.

12 Claims, 25 Drawing Sheets

(56) References Cited

U.S. PATENT DOCUMENTS

| | | |
|---|---|---|
| 5,651,781 A * | 7/1997 | Grace .............................. 606/1 |
| 2003/0065250 A1 * | 4/2003 | Chiel et al. .................... 600/115 |
| 2005/0192591 A1 | 9/2005 | Lui et al. |
| 2006/0184063 A1 | 8/2006 | Miller |
| 2008/0154296 A1 | 6/2008 | Taylor et al. |
| 2009/0018468 A1 | 1/2009 | Janssens |
| 2009/0030436 A1 | 1/2009 | Charles |
| 2010/0010499 A1 * | 1/2010 | Fischer, Jr. .................... 606/108 |
| 2010/0249505 A1 * | 9/2010 | Shoham et al. ................ 600/115 |

OTHER PUBLICATIONS

International Preliminary Report on Patentability for International Patent Application No. PCT/IB2010/000206 mailed Jul. 28, 2011.
International Search Report and Written Opinion for International Application No. PCT/IB2012/000818, mailed Jul. 27, 2012.
International Preliminary Report on Patentability for International Application No. PCT/IB2012/000818 mailed on Oct. 10, 2013.

* cited by examiner

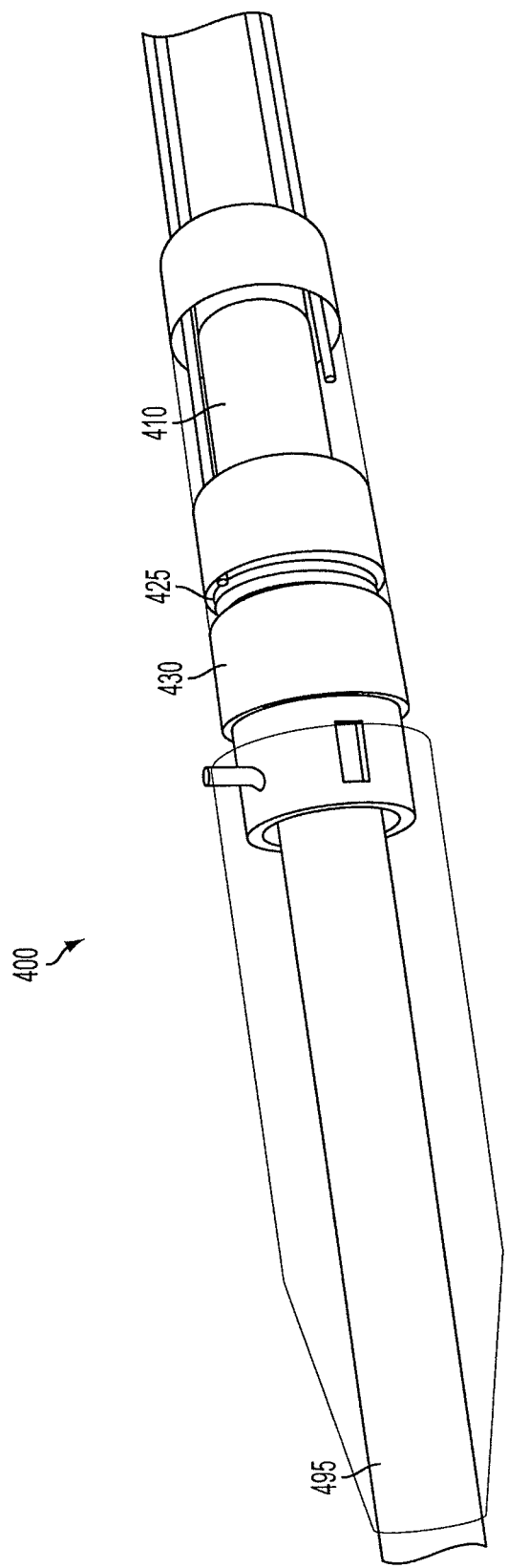

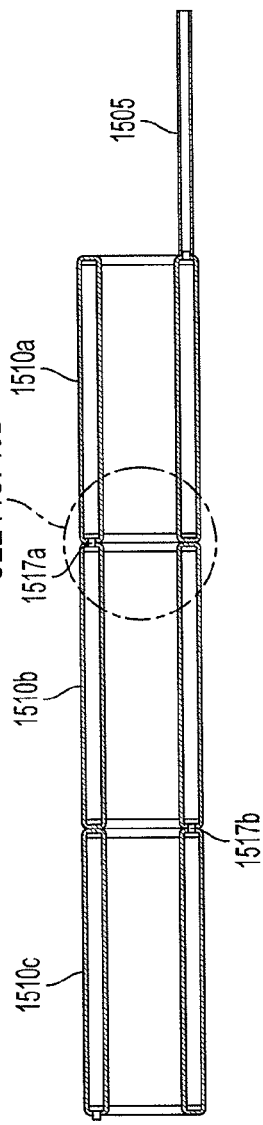
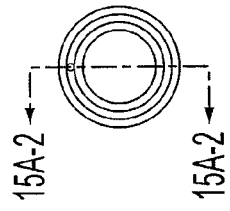
FIG. 15A-2
FIG. 15A-1
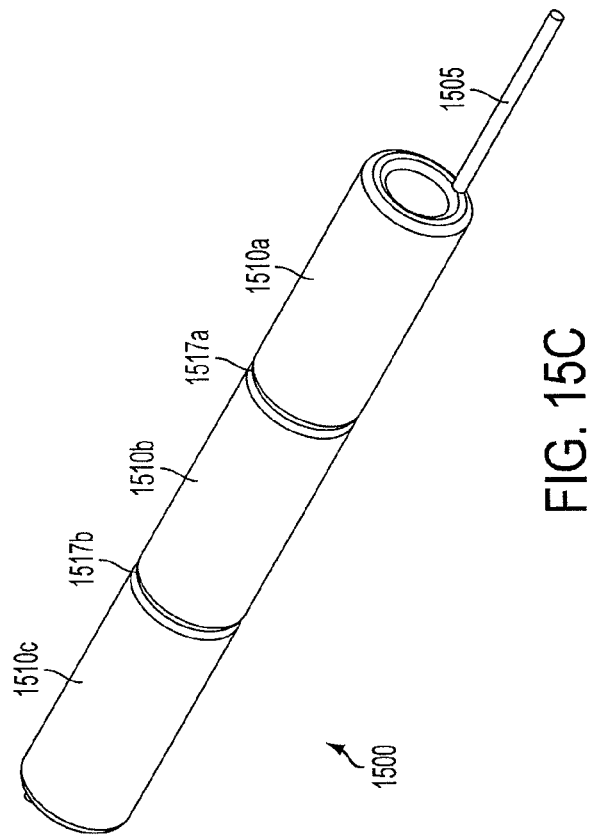
FIG. 15C
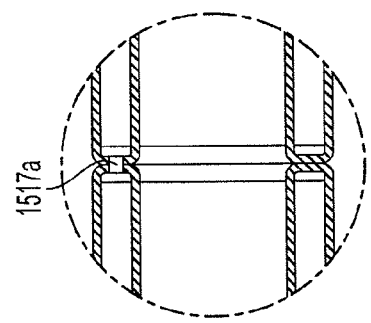
FIG. 15B

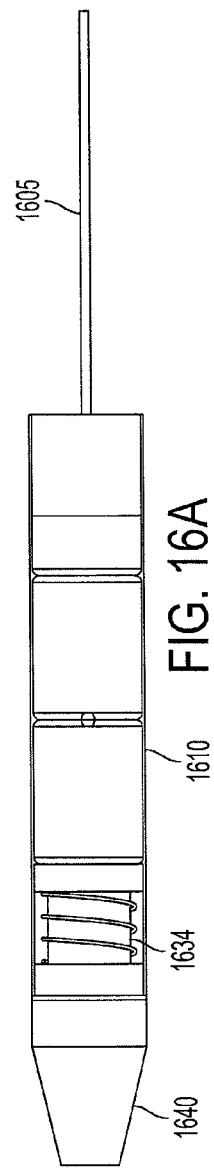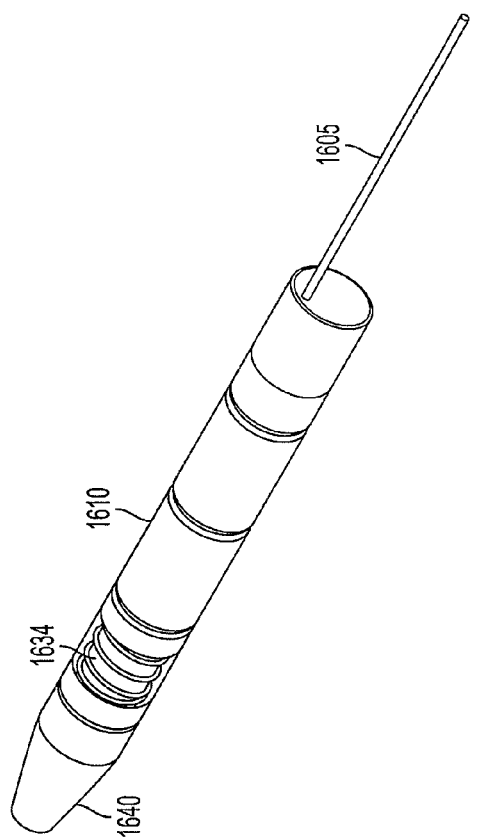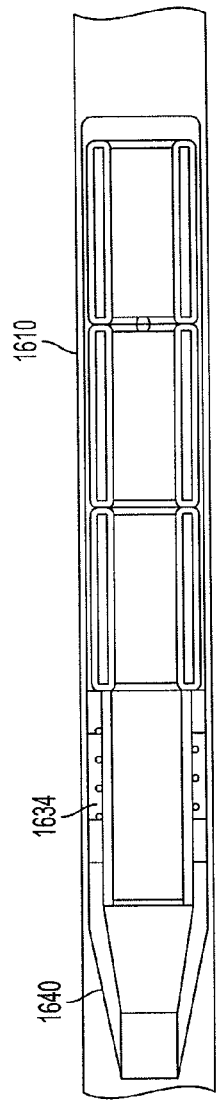

LEAD EXTRACTION METHODS AND APPARATUS

RELATED APPLICATION

This application claims priority under 35 U.S.C. §119(e) to Provisional Application Ser. No. 61/144,176, entitled "A medical device to assist in pacemaker/defibrillator electrode extraction," filed Jan. 13, 2009, which is herein incorporated by reference in its entirety.

BACKGROUND

A number of heart conditions and/or diseases are routinely treated using a pacemaker or implantable cardioverter defibrillator (ICD) that deliver electrical energy to the heart muscle to keep the patient's heart beating at a normal rhythm. Such devices are typically implanted by inserting a thin flexible wire lead into a vein to direct one or more distal electrodes into the atrium and ventricle of the heart. The lead delivers electrical energy to the heart muscle according to a desired rhythm of the heartbeat via the distal electrodes in contact with and/or anchored in the walls of the respective heart chambers. The proximal end of the lead is connected to an energy source that generates the electrical energy provided to the heart via the distal electrode(s).

FIG. 1 illustrates a schematic of one example of a pacemaker implantation. A lead 120 has a terminal connector 130c at one end and distal electrodes 130a and 130b at the other end. The lead is inserted into the right or left subclavian vein and maneuvered such that distal electrode 130a contacts the atrium wall and/or distal electrode 130b contacts the ventricle wall of the heart. The proximal end of the lead (terminal connector) is connected to an energy source 110 that provides electrical energy to the heart, via the lead 120, at a desired rhythm or pattern, which itself undergoes a subcutaneous or submuscular implantation procedure. It should be appreciated that FIG. 1 is not intended to be an accurate depiction of a pacing system, but is merely used to demonstrate the idea of device implantation. For example, the two distal electrodes are illustrated as merging into the same lead, however, multiple electrodes may each have there own independent lead connected to the energy source. Typical pacing systems may include one, two, three, four or more leads and associated electrodes. Moreover, in the dual electrode system shown in FIG. 1, one electrode may be referred to as the distal electrode and the other the proximal electrode (e.g., the tip and ring electrodes used for bipolar stimulation).

Subsequent to implant, lead 120 may need to be extracted from the body for any number of reasons. Infection caused by the pacing system (e.g., infection resulting from the implanted leads or the pacing generator pocket) is the leading reason for a physician to determine that, for the patient's safety, the lead(s) should be extracted from the body. In addition, physical damage to the lead may require lead extraction. For example, fracturing of the lead or damage to the insulation surrounding the lead may cause the device to operate non-optimally, to be altogether non-functional and/or present a risk to the patient, and therefore may require the lead to be extracted and optionally replaced. A lead left in the body from a previously removed device may need to be removed due to interference with a new lead and/or pacing device. For example, an abandoned lead may occupy intravenous space preventing a new lead from being inserted, thus requiring the abandoned lead to be removed.

Lead interaction with the body may also require the lead to be extracted. For example, excessive scar tissue at the tip of the lead may render the lead non-functional and/or may require the device to provide more energy than the device was designed to deliver. Venous obstruction by the lead causing interruption of the blood flow, interference of the lead with the circulatory system or other implanted devices, and/or pain at the site of implant all may recommend extraction of the lead. Numerous other complications may arise that cause a physician to determine that lead extraction is required for the patient's comfort, safety and/or livelihood. For example, a physician may want to replace a lead from a potentially dangerous recalled device or update an older device with a new device to exploit new technological advances.

Many conventional lead extraction devices operate by threading an expandable ("locking") wire through the lumen of the lead. Standard pacemaker leads are formed from a coiled wire having a hollow center (lumen) along the axis of the lead. The lead lumen may be used to assist in extracting the lead from the body. Such lead extraction devices typically operate by having a guide wire with an outer diameter less than the inner diameter of the lead threaded through the lumen until it reaches the distal end (e.g., the location in which the lead is anchored into the ventricle or atrium wall of the heart).

The guide wire may be provided with a distal portion that can be expanded to engage and grip the internal wire coil of the lead. For example, the distal end of the guide wire may include a coil of wire that can be unwound from the proximal side of the guide wire once the guide wire has reached the distal end (e.g., the implantation end) of the lead. As the wire unwinds, it tangles with the internal wire coil of the lead to anchor the distal end of the guide wire. The guide wire may then be pulled out, extracting the lead along with it.

However, lead extraction may be complicated by tissue adhering to the outer surface of the lead. For example, after the lead has been implanted, scar tissue may form around the lead at any number of different sites (e.g., the insertion point of the lead into the vein or at any location along the vein and/or heart wall) making it difficult for a surgeon to extract the lead without tearing the surrounding tissue. Moreover, if more than one lead is present in the vein, the leads can become attached to one another creating a relatively complicated extraction procedure that is often problematic using conventional lead extraction devices. Lead extraction devices that utilize the internal lumen of the lead for extraction do not address the problem of fibrous tissue attached to the external portion of the lead and may therefore be rendered ineffective, or are used with significant risk of tearing critical internal blood vessels and causing dangerous, and sometimes fatal, damage to the patient should the lead be extracted using excessive force.

To address issues related to tissue adhering to the outside circumference of the lead, conventional methods and devices have used various relatively rudimentary manual devices that cut the surrounding tissue with a knife or edged implement operated by a surgeon and/or utilize laser or diathermic devices that provide laser or electrical energy to cut the surrounding tissue to release the lead for extraction. For example, a hollow sheath having a cutting portion on the distal end may be threaded over the lead. A surgeon may then manually forced the sheath forward so that the cutting portion engages the attached tissue and cuts the tissue away from the lead. The surgeon may also manually rotate the sheath to facilitate cutting and or use a trigger gun that attaches to the sheath and that rotates the sheath when the trigger is engaged. In some embodiments, laser or diathermic devices are affixed to the cutting portion of the lead to ablate the tissue to assist in separating surrounding tissue from the lead.

SUMMARY

Some aspects of the invention derive from Applicant's appreciation that utilizing pressure changes to semi-automate or fully-automate at least part of the lead extraction process may result in simpler, safer and more effective lead extraction procedures. For example, one or more hydraulic and/or pneumatic techniques may be used to anchor and/or advance a lead extraction device along a lead and/or facilitate separating tissue from the lead or separating two leads from one another. The term anchor or anchoring is used herein to describe the function of applying force/pressure that tends to resist motion of at least one part, portion or component in at least one direction.

Some embodiments include a device for assisting in removing an implanted lead, the device comprising a body portion having a center adapted to accommodate the lead, a cutting component coupled to the body portion to assist in separating tissue from the lead, and at least one anchoring component disposed at least partially within the body portion, the at least one anchoring component capable of providing pressure on the lead that resists movement of at least part of the body portion along the lead at least in part by applying fluid pressure.

Some embodiments include a device for assisting in removing an implanted lead, the device comprising means for accommodating the lead via a center portion of the device, means for separating tissue from the lead, and means for providing pressure on the lead to resist movement of at least part of the device along the lead at least in part by applying fluid pressure.

Some embodiments include a method of operating a device adapted to assist in removing an implanted lead, the method comprising anchoring a first portion of the device at least in part by applying fluid pressure, advancing a second portion of the device along the lead at least in part by applying fluid pressure, releasing the first portion of the device, and advancing the first portion of the device along the lead.

BRIEF DESCRIPTION OF THE DRAWINGS

FIGS. 4A-4F illustrate a number of stages of an operation cycle of a lead extraction device, in accordance with some embodiments of the present invention;

FIGS. 15A, 15B and 15C illustrate different views of a chain of balloons capable of both anchoring and advancing a lead extraction device, in accordance with some embodiments of the present invention;

FIGS. 16A, 16B and 16C illustrate views of a lead extraction device incorporating at least some anchoring/advancing techniques discussed in connections with FIGS. 13-15, in accordance with some embodiments of the present invention;

DETAILED DESCRIPTION

As discussed above, most conventional lead extraction techniques rely either on rudimentary manual cutting devices or laser or diathermic devices that ablate surrounding tissue using laser or electrical energy. Drawbacks of conventional manual cutting devices include that the manual devices are often awkward and difficult to operate, placing a relatively heavy burden reliance on the dexterity of the physician and increasing the risk of complicating the procedure. In particular, operating the cutting blade and advancing the device forward to completely release the lead may be considerably difficult, often leading to excessive tissue damage, further complications and/or increasingly invasive surgical procedures to extract the lead. Laser or diathermic devices may provide some improvements with respect to the complexity and success rate of lead extraction over conventional manual extraction devices, however, the equipment is relatively expensive and may not be available to surgeons performing such procedures.

Applicant has appreciated that utilizing pressure changes to semi-automate or fully-automate at least part of the lead extraction process may result in simpler, safer and more effective lead extraction procedures. For example, one or more hydraulic and/or pneumatic techniques may be used to advance a lead extraction device along a lead. According to some embodiments, fluid pressure changes are used to inflate/deflate one or more balloons, tubes or other components, to anchor and/or advance the device over the lead and/or to cut/separate tissue from the lead. As used herein, the term inflate describes the operation of increasing fluid pressure and the term deflate describes the operation of decreasing fluid pressure. The term fluid is used herein to describe gases, liquids and some solids (e.g., foams or other solids that can be used to effect pressure changes). According to some embodiments, anchoring, advancing and cutting is achieved utilizing fluid pressure techniques.

Following below are more detailed descriptions of various concepts related to, and embodiments of, methods and apparatus according to the present invention. It should be appreciated that various aspects of the invention described herein may be implemented in any of numerous ways. Examples of specific implementations are provided herein for illustrative purposes only. In addition, the various aspects of the invention described in the embodiments below may be used alone or in any combination, and are not limited to the combinations explicitly described herein.

Figure 1:
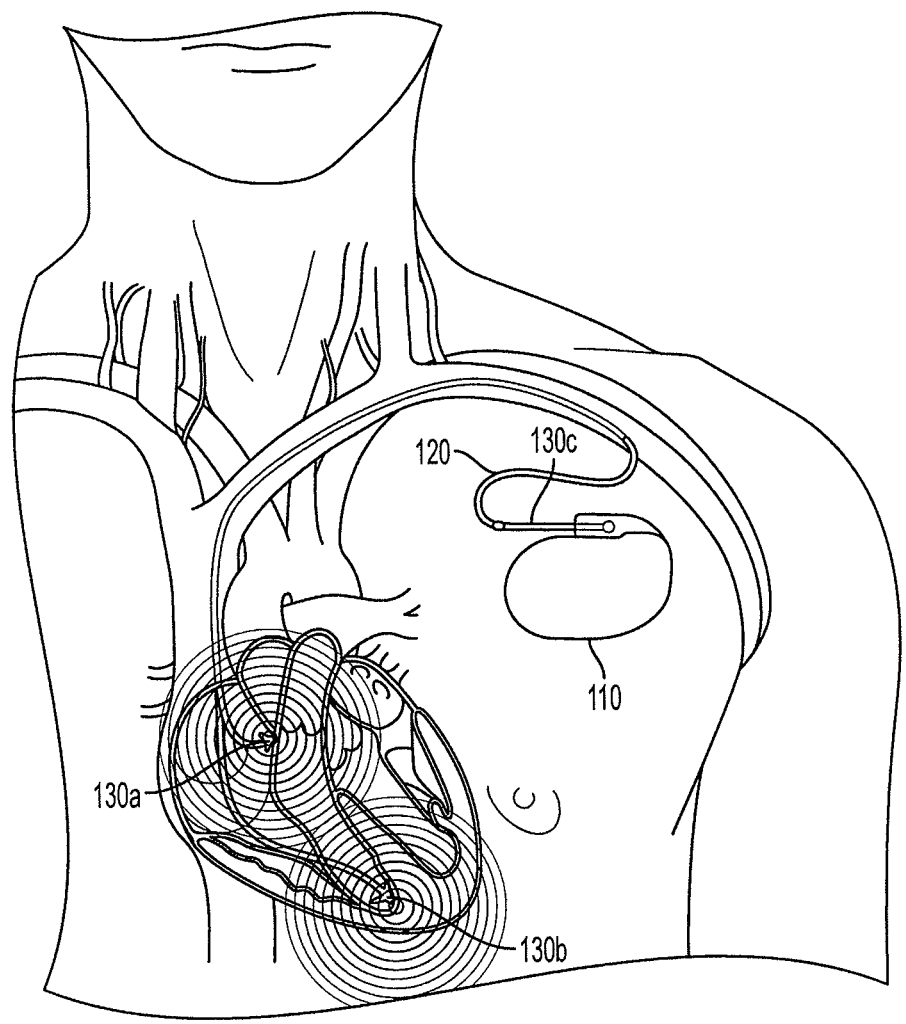
FIG. 1 illustrates an implanted pacing system.
Figure 2:
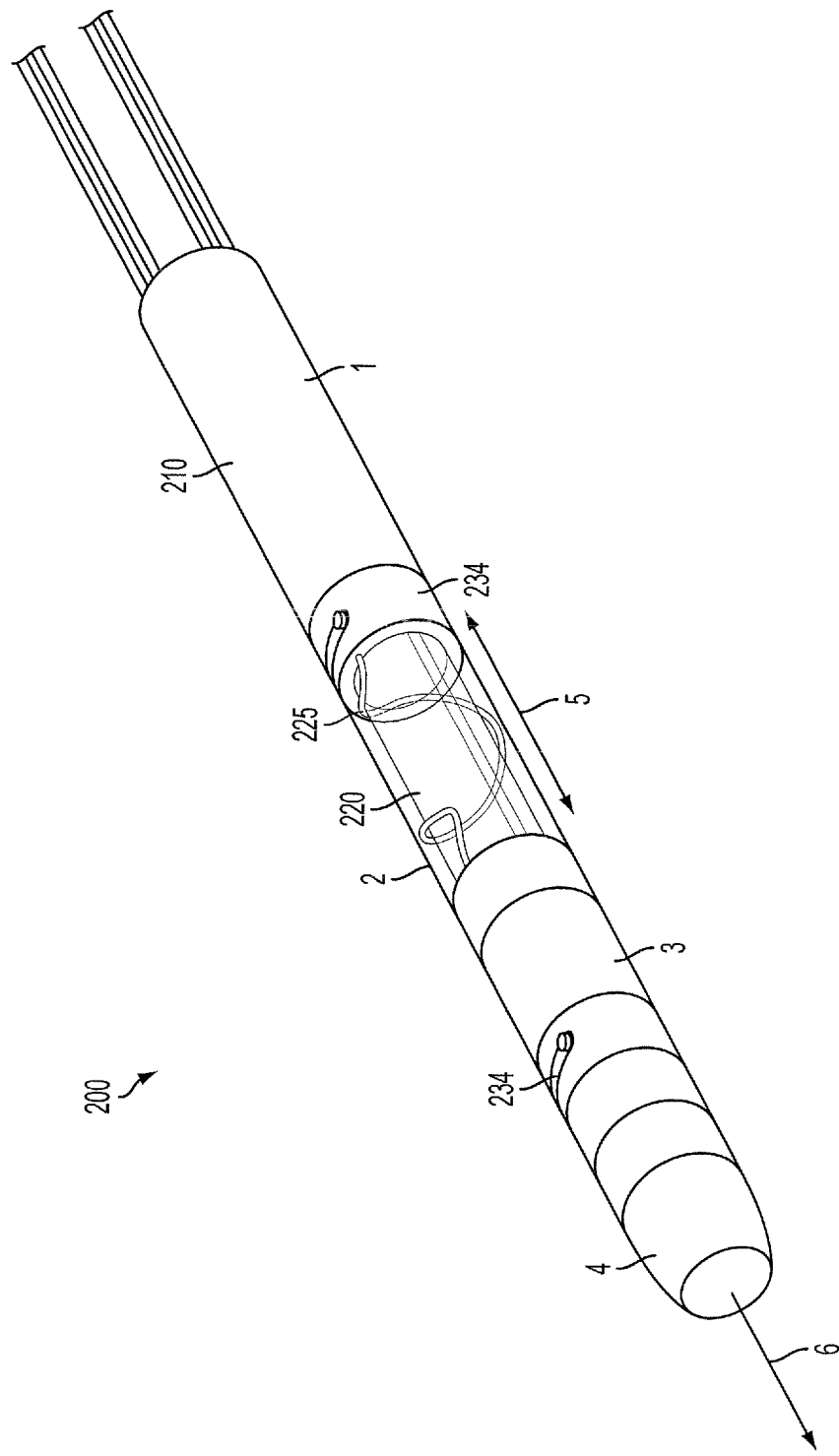
FIG. 2 illustrates a lead extraction device to assist in lead removal, in accordance with some embodiments of the present invention.

FIG. 2 illustrates a lead extraction device in accordance with some embodiments of the present invention. Device 200 comprises a body 5 having a hollow central axis that is at least wide enough to accommodate a heart lead. The body includes a proximal portion 1, an expansion portion 2, a distal portion 3 and a cutting portion 4. Cutting portion 4 may be positioned at a distal end of the device (e.g., at one end of distal portion 3) and may be, for example, a circular blade having an opening designed to accommodate a lead and capable of cutting tissue that has grown on the lead as the device is advanced along the lead in the direction indicated by arrow 6.

In some embodiments, cutting portion 4 rotates as the device advances along the lead to facilitate separating the lead from any tissue that has grown on, or otherwise adhered to the lead, and or two separate two leads from one another. In other embodiments, the blade does not rotate and tissue separation is performed by the cutting portion being advanced along the lead, as discussed in further detail below. The cutting portion may rotate and advance simultaneously or rotation and advancement may be two separate and independent motions. The rotation of the cutting portion may be in a single direction (e.g., clockwise rotation) or may rotate both clockwise and counterclockwise in alternation. The cutting portion may fully rotate or may affect only partial rotation, as the aspects of the invention are not limited for use with any particular cutting mechanism.

Proximal portion 1 may be located at the opposite end of the device from the cutting blade and may contain one or more anchoring balloons 210 adapted to grip the lead when inflated. In some embodiments, the anchoring balloon is torus shaped such that when deflated a lead can pass through the center of the torus unimpeded and when inflated the balloon constricts and grips the lead to anchor the device, as discussed in further detail below. The term "balloon" refers herein to any structure or combination of structures, having one or more portions that vary under fluid pressure. For example, a balloon may include structure(s) having one or more portions capable of being inflated and/or deflated using forced fluid (e.g., forced air, liquid or solid such as foam). A balloon can be a single component or formed from multiple components depending on what effect is desired upon inflating/deflating the balloon (e.g., elongation, constriction, anchoring, etc.).

Figure 3A:
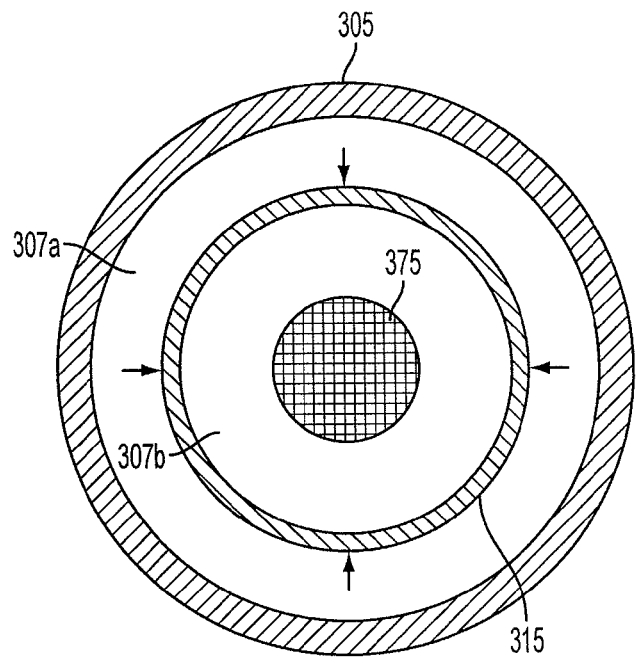
FIGS. 3A and 3B illustrate an example of one type of anchoring balloon in the deflated and inflated states, respectively, in accordance with some embodiments of the present invention.
Figure 3B:
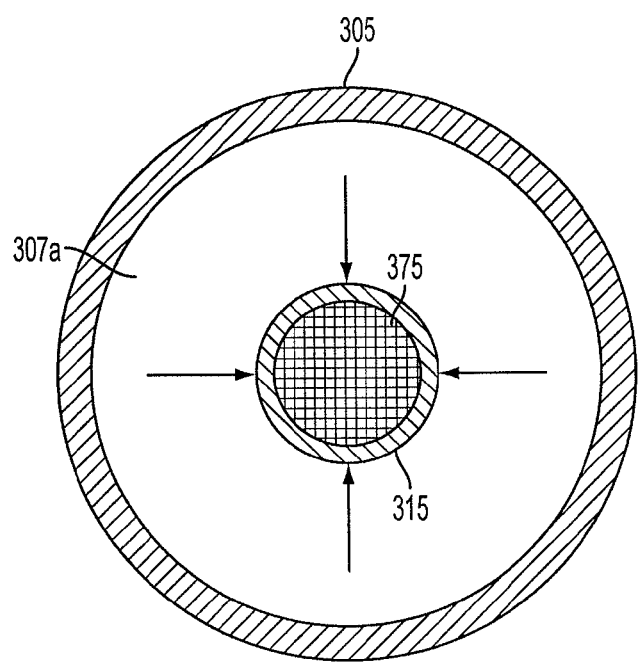

FIGS. 3A and 3B illustrate a cross-section of an anchoring component (e.g., an anchoring balloon) in both the deflated and inflated states, respectively, in accordance with some embodiments of the present invention. In FIGS. 3A and 3B, the anchoring component includes a balloon comprised of an outerl tube 305 formed from a relatively rigid material (e.g., a steel, silicone or polymer tube) and an inner tube formed from a relatively elastic material (e.g., silicone, nylon, polymer or other materials by which medical balloons and/or tubing are formed).

In the deflated state illustrated in FIG. 3A, a gap 307a may exists between the outer and inner tube whereby the pressure within the gap permits the inner tube to relax such that there is a gap 307b between the inner tube 315 and the lead 375 and/or sufficient space or lack of resistance between inner tube 315 and lead 375 such that the anchoring component is capable of movement along the length of the lead. Inflating the anchoring component may include forcing fluid (e.g., air, liquid, etc.) into gap 307a causing increased pressure to be exerted on the inner tube. Because the outer tube is relatively rigid and resistant to expansion, the increased pressure causes the inner tube to depress inwards to grip the lead and fix the anchoring component relative to the lead, as illustrated in FIG. 3B. In particular, gap 307 expands under the increased pressure caused by fluid inflating pressing the inner tube towards the lead and causing gap 307b to decrease and/or be entirely removed as the inner tube constricts around the lead.

Figure 3C:
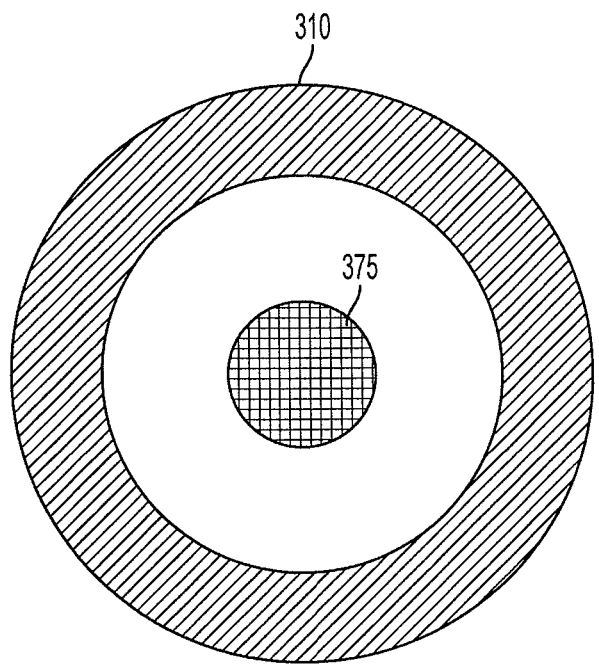
FIGS. 3C and 3D illustrate an example of one type of anchoring balloon in the deflated and inflated states, respectively, in accordance with some embodiments of the present invention.
Figure 3D:
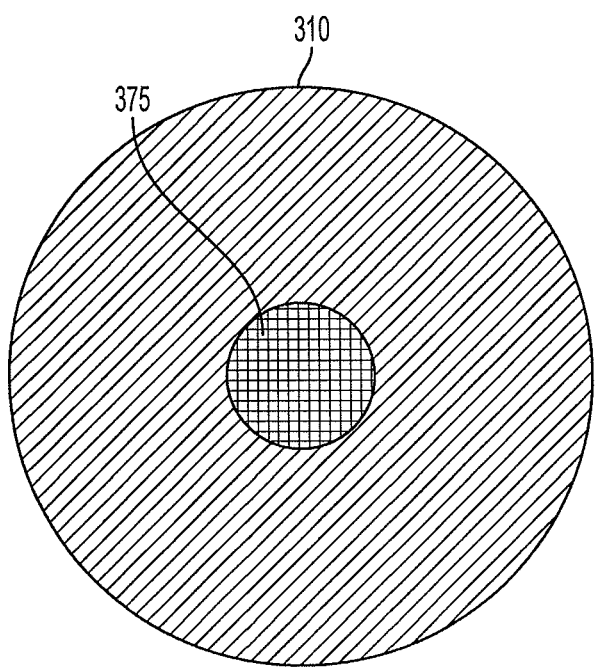

FIGS. 3C and 3D illustrate a cross-section of an anchoring balloon in both the deflated and inflated stages, respectively, in accordance with alternative embodiments. Balloon 310 may be a torus shaped balloon that forms a central hole that, when the balloon is deflated, has a diameter that can accommodate the heart lead and allow relative movement between the lead and the balloon. As illustrated in FIG. 3C, balloon 310 is deflated and lead 375 passes through the center of the balloon relatively unimpeded as the inner wall of the balloon does not grip lead, thus allowing the balloon to slide up or down the lead. In FIG. 3D, balloon 310 has been inflated such that the inner wall of the balloon grips the lead and the friction therebetween prevents motion of the balloon relative to the lead. That is, inflation causes fluid to fill the balloon, simultaneously reducing the size of the center hole until the inner wall grips the lead. The anchoring balloons need not be designed to accommodate the lead through a center of the balloon. For example, a balloon may be disposed over, under or to the side of a lead such that when the balloon is inflated, the balloon applies pressure to the lead such that the balloon resists relative movement between the lead and some portion of the lead extraction device.

It should be appreciated that the expansion of balloon 310 in an outward direction may be substantially prevented, for example, by providing the balloon inside a relatively rigid tube (e.g., the body or outer tube of the lead extraction device) such that expansion of the balloon outward is prevented and inflation results primarily or substantially in inward constriction of the center hole. The relatively rigid tube may be formed from any material such as metal, plastic, polymer, silicone or any other suitable material. Outward expansion of the balloon may be prevented in other ways, as the aspects of the invention are not limited in this respect.

While the balloon illustrated in FIGS. 3C and 3D are toroidal in shape, it should be appreciated that the anchoring balloon may be of any shape capable of gripping and releasing a lead. Other methods of achieving anchoring using pressure changes may be used as well, as the aspects of the invention are not limited in this respect. It should be appreciated that the cross-sections of the anchoring balloons in FIGS. 3A-3D are merely schematic to illustrate principles of anchoring via balloon inflation. The dimensions illustrated are not meant to depict actual absolute or relative dimensions.

Referring back to FIG. 2, expansion portion 2 includes a spring mechanism 225 and an elongation component 220 (e.g., one or more elongation balloons). Spring mechanism 225 connects the proximal portion with the distal portion and an elongation balloon 220 is arranged to stretch the spring when inflated and allow the spring to return to repose when deflated. The elongation component may be formed from and inner tube and an outer tube, both of which may be relatively flexible. The inner tube and the outer tube may be connected to each other at each end (e.g., at the end where the expansion portion connects to the proximal portion and at the end where the expansion portion connects to the distal portion).

Inflating the space between the inner tube and the outer tube causes the elongation component 220 to expand, thereby stretching the spring and increasing the distance between the proximal portion and distal. When the space is deflated, the spring relaxes and returns to repose, thereby reducing the distance between the distal and the proximal portions of the device. Spring mechanism 225 may be any type of component such as a standard spring or an accordion type material that can be elongated under fluid pressure.

Distal portion 3 may include one or more distal anchoring balloons (or any other type of anchoring mechanism) arranged to grip the lead at the distal end of the device. The one or more distal anchoring balloons may be similar in construction and operation to the anchoring balloons described in connection with FIGS. 3A-3D, or may be any other type of component capable of gripping and releasing the lead under fluid pressure as desired, as the aspects of the invention are not limited in this respect. Device 200 may also include a rotation component 234 coupled to the cutting portion to cause the cutting portion to rotate as the device advance forward along the lead. In FIG. 2, rotation component 234 has a member on both the proximal and distal end of the device to effect rotation and may use a slot and pin mechanism, as discussed in further detail below. Other types of rotation mechanisms may also be used (some embodiments of which are also discussed below), as the aspects of the invention are not limited for use with any particular type of rotation component.

FIGS. 4A-4F illustrates the internal components of a lead extraction device (e.g., the internal components of lead extraction device 200 illustrated in FIG. 2) at each of a number of stages of an extraction operation cycle that advances the device over the lead and separates the lead from any attached tissue that may prevent the removal of the lead, according to some embodiments. Similar to device 200, device 400 includes a proximal anchor balloon 410, an expansion balloon 420, a distal anchoring balloon 430 and a spring 425 that connects the distal and proximal portions of the device. Device 400 is shown inserted over a lead 495, for example, by a surgeon that threads the exposed end of the lead through the central axis of the sheath.

Figure 4A:
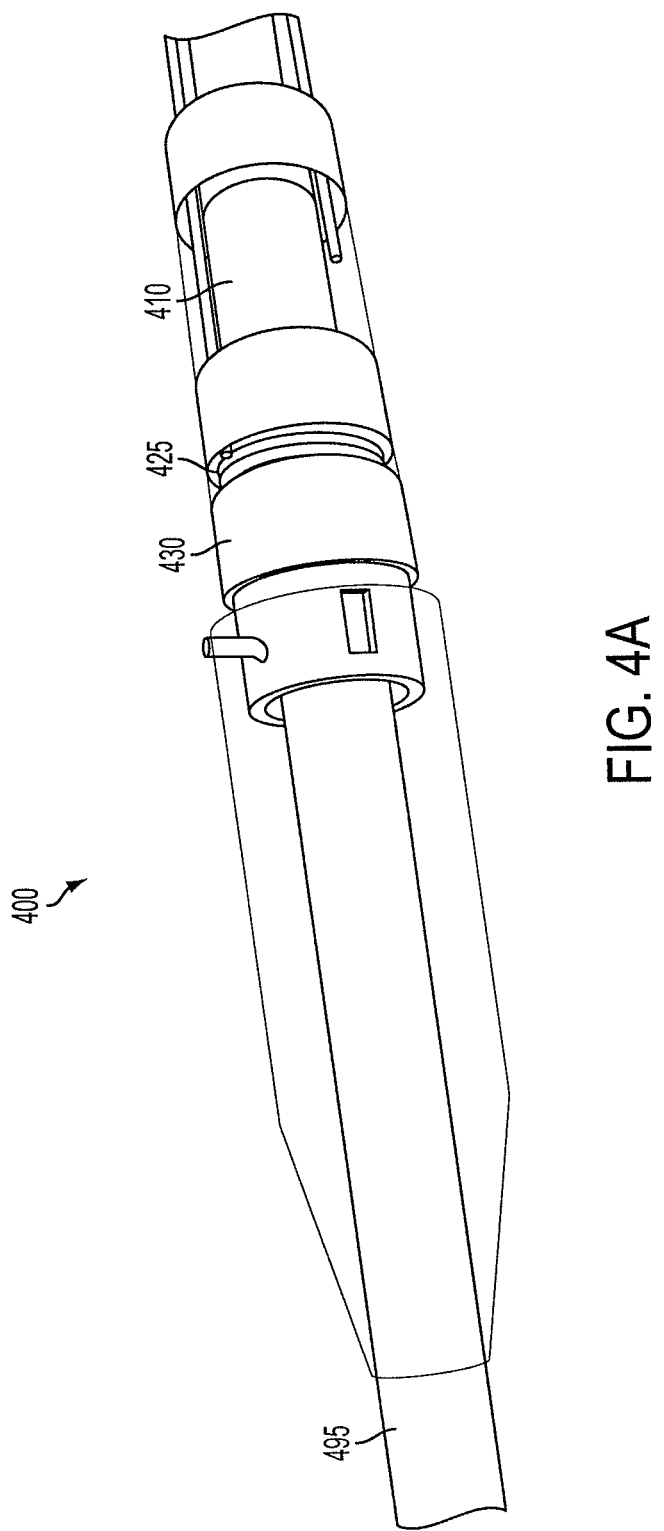

FIG. 4A illustrates a first stage of an operation cycle of the lead extraction device after the device has been placed on the lead. In the first stage, all of the balloons may be deflated. In particular, anchoring balloons 410 and 430 are deflated such that the device is free to slide along the lead (i.e., the lead can pass through the center of the sheath relatively unimpeded by either anchoring balloons. This stage allows the surgeon to thread the lead through the center of the sheath and position the device for extraction of the lead. In addition, the expansion balloon 420 may also be deflated such that spring 425 is in repose and the distal and proximal portion are as close together as the spring will allow. From this stage, the device is ready to begin extracting the lead.

Figure 4B:
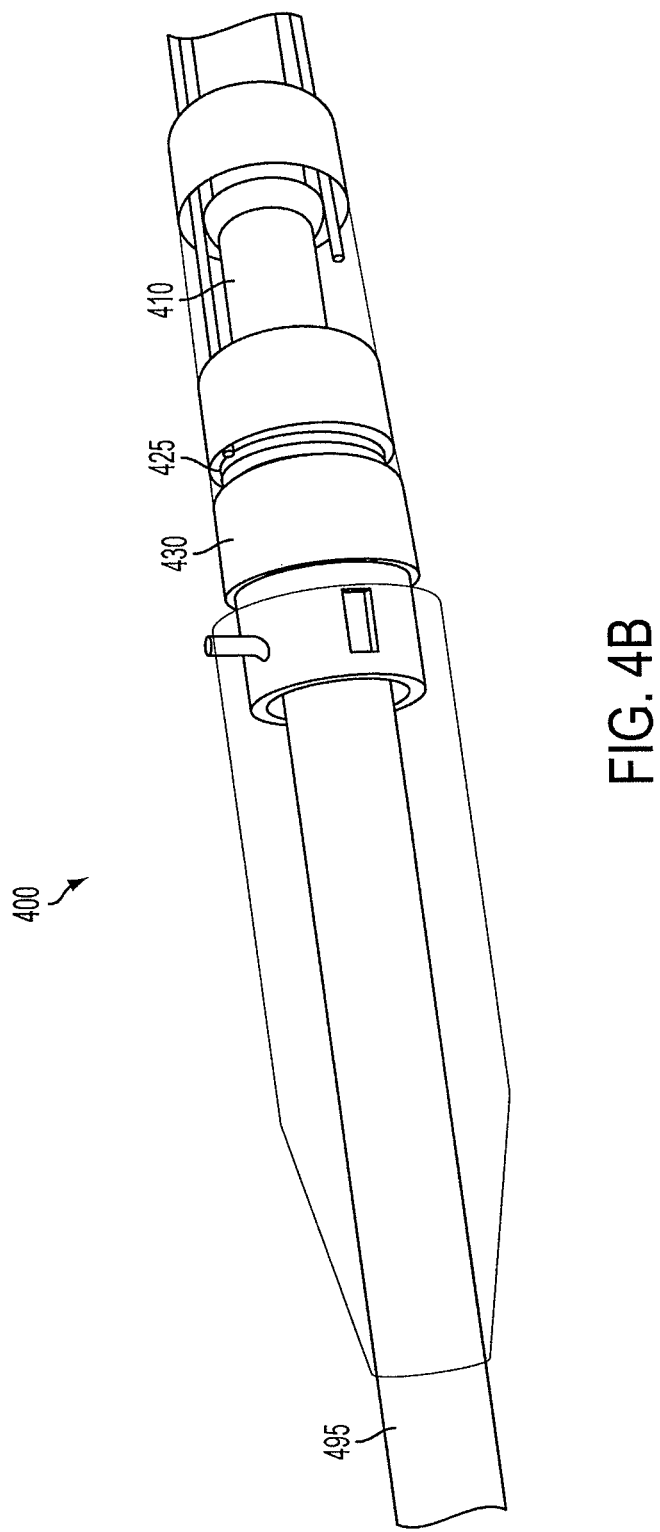

FIG. 4B illustrates a second stage of the operation cycle of the lead extraction device. In the second stage, the proximal anchoring balloon 410 is inflated such that the balloon grips the lead and anchors the proximal portion of the device such that motion of the proximal portion relative to the lead is prevented. For example, the proximal anchoring balloon 410 may transition from deflated (e.g., as shown in FIG. 3A) to inflated (e.g., as shown in FIG. 3B) such that the inner tube is pressed inward to grip the lead. Alternatively, proximal anchoring balloon 410 may be implemented as the torus shaped balloon described in connection with FIGS. 3C and 3D, such that inflation causes the center hole to constrict around the threaded lead.

Figure 4C:
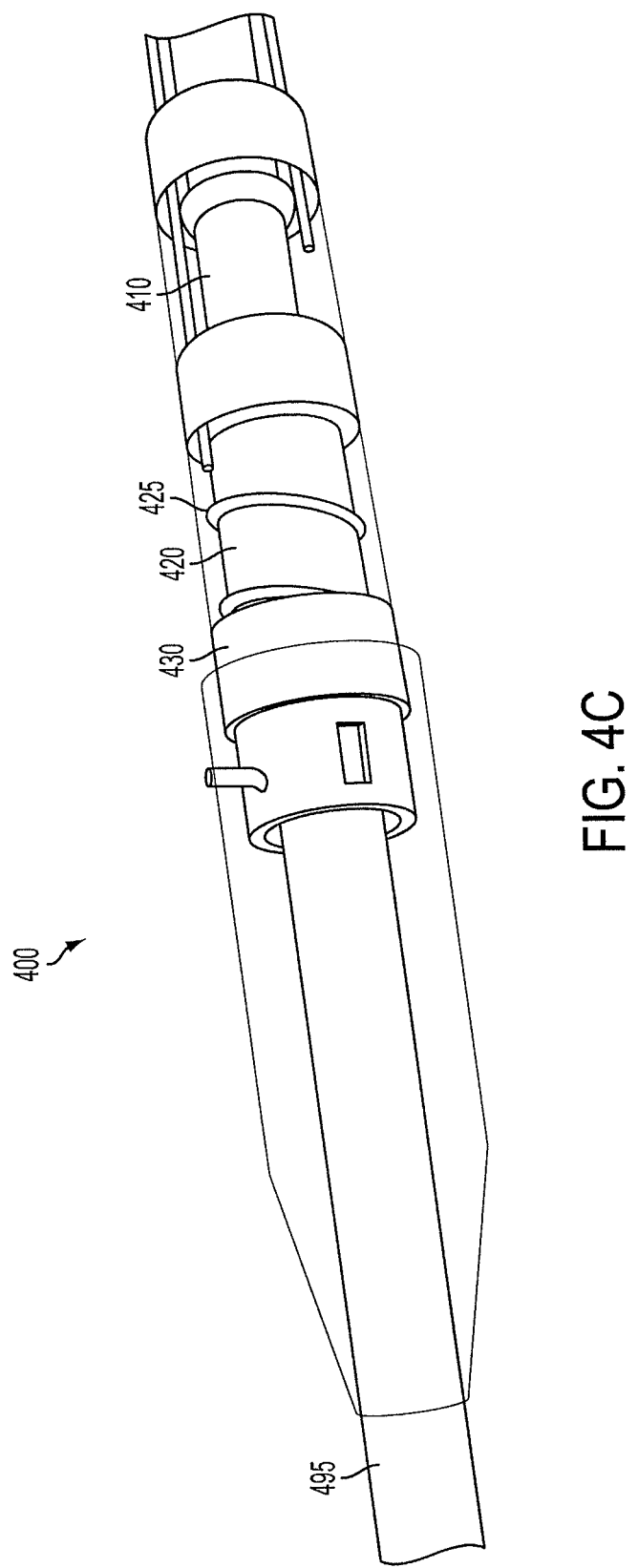

FIG. 4C illustrates a third stage of the operation cycle that advances the distal portion of the device forward along the lead, separating tissue that may be attached to the lead. In this third stage, the elongation balloon 420 is inflated to stretch spring 425. Since the proximal portion of the device is anchored by inflated anchoring balloon 410, the spring forces the distal portion forward along the lead as the spring is stretched by elongation balloon 420. The forward force on the distal portion causes the cutting portion to advance along the lead and cut tissue attached to the lead to prepare the lead for extraction. In some embodiments, the forward force also rotates the cutting portion to facilitate separating the tissue from the lead, as discussed in further detail below.

Figure 4D:
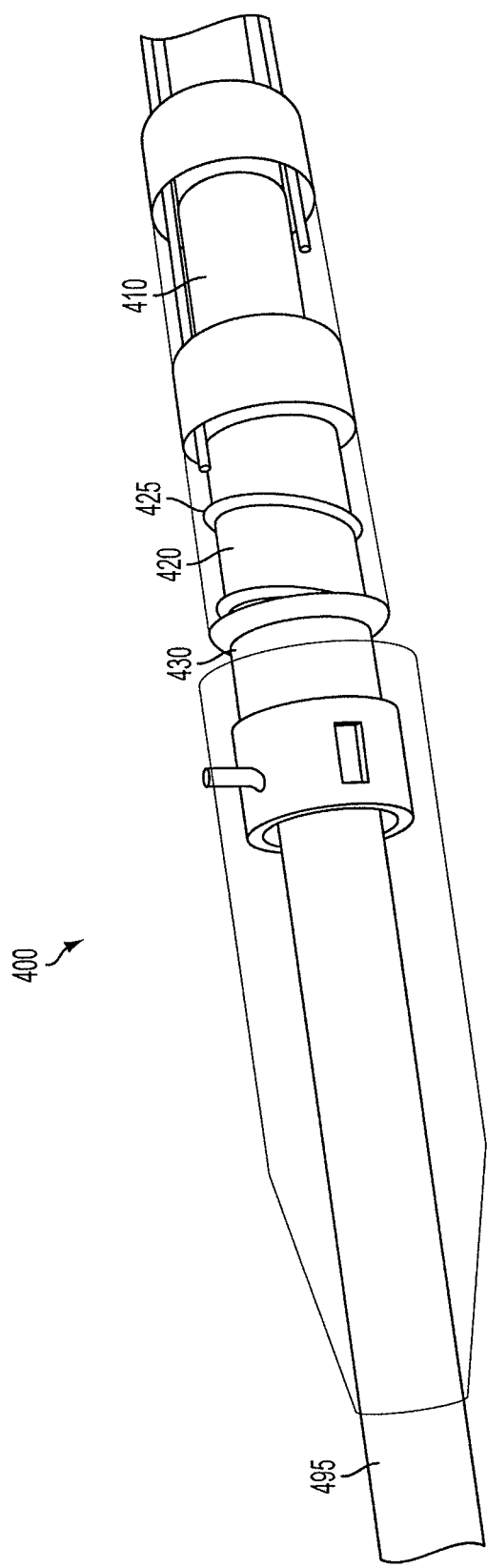

FIG. 4D illustrates a fourth stage of the operation cycle that anchors the distal portion of the device to the lead. After the distal portion has been advanced along the lead, the distal anchoring balloon 430 may be inflated to grip the lead. Anchoring balloon 430 may operate in a same or similar manner as the proximal balloon 410 describe above. At this stage, both the proximal and distal portions of the device are anchored to the lead and the spring 425 is stretched by the inflated elongation balloon 420. It should be appreciated that anchoring balloon 430 may include an inflation tube or other inflation mechanism, although no such mechanism is illustrated in FIGS. 4A-4F. Alternatively, anchoring balloon 430 may be replaced with an anchoring component that applies a substantially constant resistance to movement relative to the lead such that inflation/deflation of the distal anchoring component is not necessary, some embodiments of the which are discussed in further detail below.

Figure 4E:
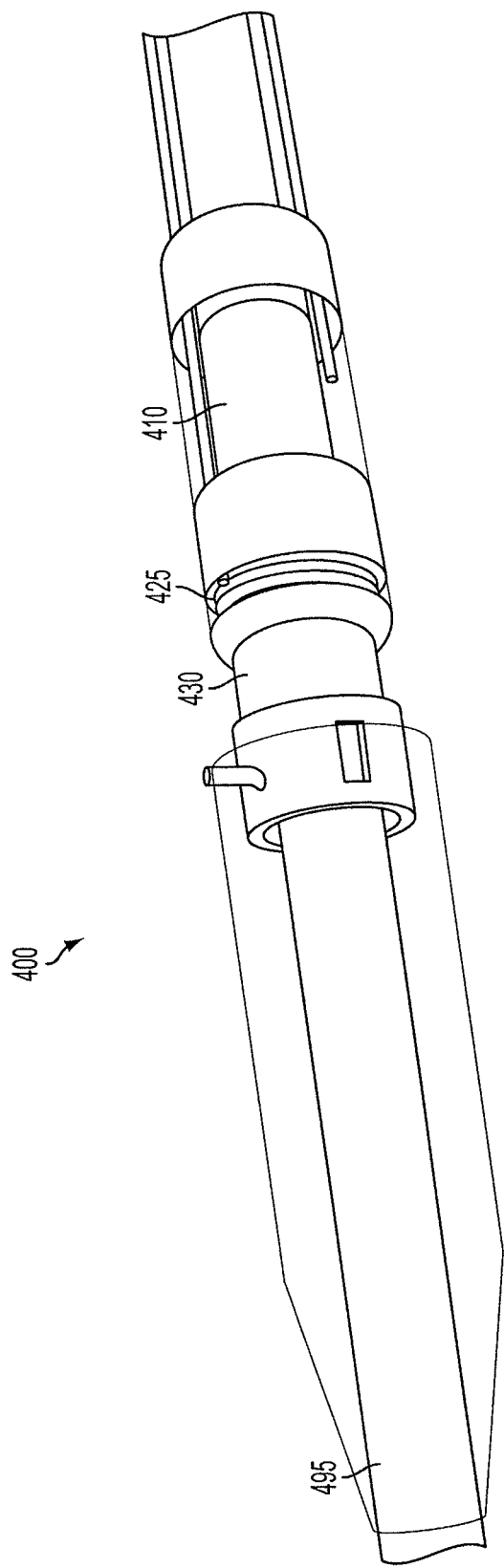

FIG. 4E illustrates a fifth stage of the operation cycle wherein the elongation balloon 420 is deflated causing the spring 425 to tend to relax back to repose. Subsequent to or simultaneously with deflating the elongation balloon 420, proximal anchoring balloon 410 is also deflated. Because the distal anchoring balloon 430 is inflated, the force of the contracting spring as it returns to repose pulls the proximal portion of the device (now released due to the deflation of the proximal anchoring balloon 410) forwards to advance the proximal portion of the device along the lead. The distal anchoring balloon may then be deflated to return the device to the first stage. That is, all balloons may be deflated and the device returns to its initial configuration but has been advanced along the lead, separating (or at least partially cutting/separating) tissue that the cutting portion may have encountered during the incremental advancement of the operation cycle (see e.g., FIG. 4F).

The stages may be repeated to continue to advance the device forward until the device has advanced as far as it needs to advanced in order to release the lead so that it can be pulled from the body. It should be appreciated that the various stages need not be performed sequentially and portions of the stages or entire stages may be performed simultaneously and/or may overlap in time, as the aspects of the invention are not limited for use with any particular timing scheme.

The lead extraction devices described above embody a number of general concepts that facilitate advancing a lead extraction device along a lead while separating tissue that has attached to the lead and/or separating the lead from another lead to which is has adhered. For example, the lead extraction devices describe above illustrate examples of how a lead extraction device can be internally advanced using applied pressure changes, including using applied pressure changes to anchor, advance and/or cut. It should be appreciated that anchoring, advancing and cutting can be implemented in a variety of different ways, some embodiments of which are described in further detail below. It should be further appreciated that implementations embodying the concepts of anchoring, advancing and cutting may be used alone or in any combination, as the aspects of the invention are not limited to the specific combinations specifically illustrated herein.

In some embodiments, the distal anchoring component is formed from a constant friction component, rather than an inflatable/deflatable anchoring component (e.g., the inflatable/deflatable anchoring balloons illustrated in FIGS. 3A-3D). For example, the distal anchoring component may provide a constant friction to the lead that is greater than the resistance of the proximal anchoring component on the lead when it is not engaged (e.g., deflated) and less than the resistance of proximal anchoring component on the lead when it is engaged (e.g., when inflated), as discussed in further detail below.

Figure 5:
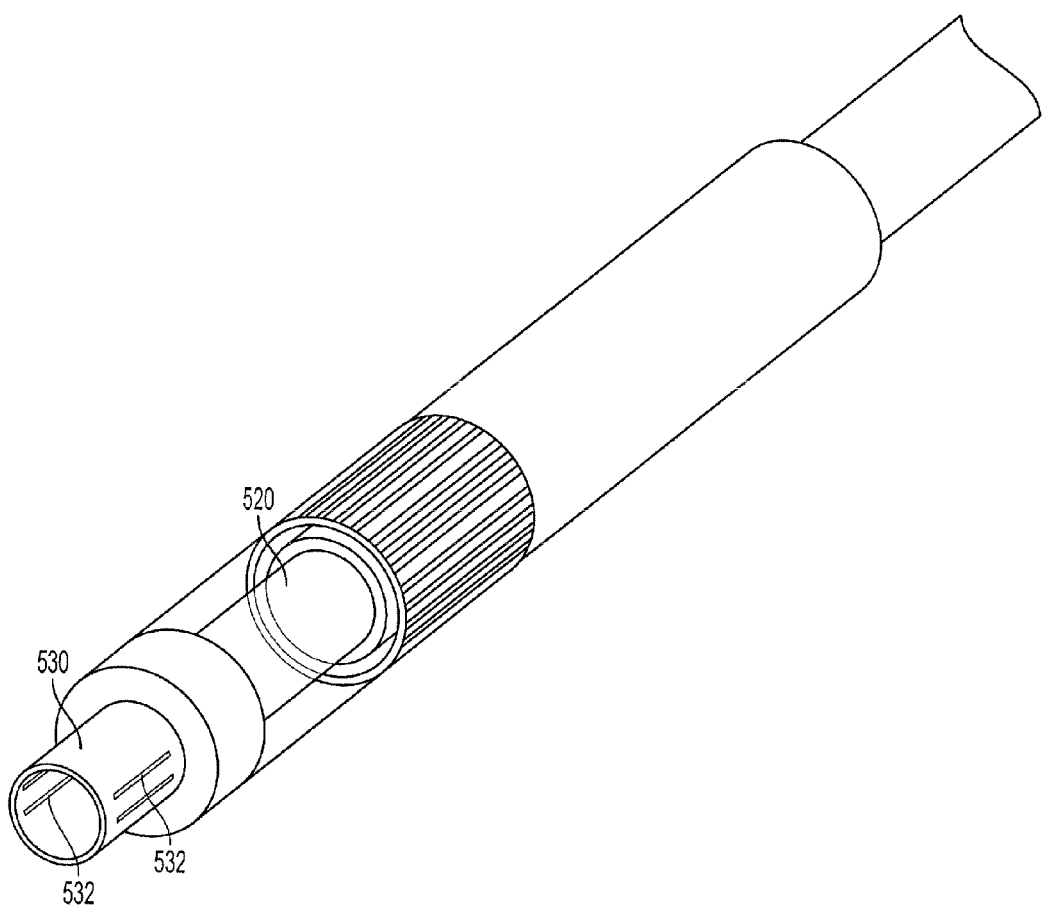
FIG. 5 illustrates a portion of a lead extraction device comprising a distal anchoring component having a constant friction portion, in accordance with some embodiments of the present invention.

FIG. 5 illustrates a distal anchoring component having a constant friction portion, in accordance with some embodiments of the present invention. Proximal anchoring component may be any of the anchoring components described herein being capable of anchoring and releasing a lead as desired due to fluid pressure changes. Similarly, expansion component 520 may include any of the mechanisms described above for elongating the distance between the proximal and distal portions of the lead extraction device (e.g., one or more elongation balloons). Distal anchoring component 530 may be a constant friction component that applies a substantially constant friction on the lead.

Distal anchoring component 530 may be a relatively rigid tube having a portion that is bent inwards to contact the lead to apply a constant friction. For example, the rigid tube may have one or more perforated tabs 532 that can be pressed inward to pinch the lead to provide a desired resistance against motion along the lead. In an alternative embodiment, the constant friction component may be formed by twisting a spring that contacts the lead at desired locations and pressure to apply a substantially constant friction to the lead.

As discussed above, the distal anchoring component may have a substantially constant resistance that is greater than the resistance of the proximal anchoring component when the proximal anchoring component is not engaged and less than the resistance of the proximal anchoring component when the proximal anchoring component is engaged. Thus configured, when the proximal anchoring component is engaged with the lead and the elongation component is inflated to stretch the spring mechanism, the distal portion is forced forward to advance along the lead because the proximal anchoring component provides greater resistance against movement relative to the lead despite the constant friction of the distal anchoring component. When the elongation component and the proximal anchoring component are deflated, the constant friction component provides greater resistance against movement such that as the spring mechanism returns to repose, the proximal portion (disengaged) is pulled towards the distal portion to advance the device along the lead.

A purpose of some embodiments of a lead extraction device is to separate tissue that has grown on or attached itself to the lead to facilitate lead removal without unnecessarily tearing and/or damaging the surrounding tissue. As discussed above, separation may be performed by providing a cutting portion (e.g., a knife or blade) having one or more edges designed to cut tissue to help in separating tissue from the lead. In some embodiments, the forward motion of the lead extraction device provides the force to separate tissue from the lead. However, in other embodiments, the cutting capabilities of the lead extraction device may be improved by adding rotation in addition to forward motion. A number of non-limiting embodiments of rotating cutting portions are described in further detail below.

Figure 6A:
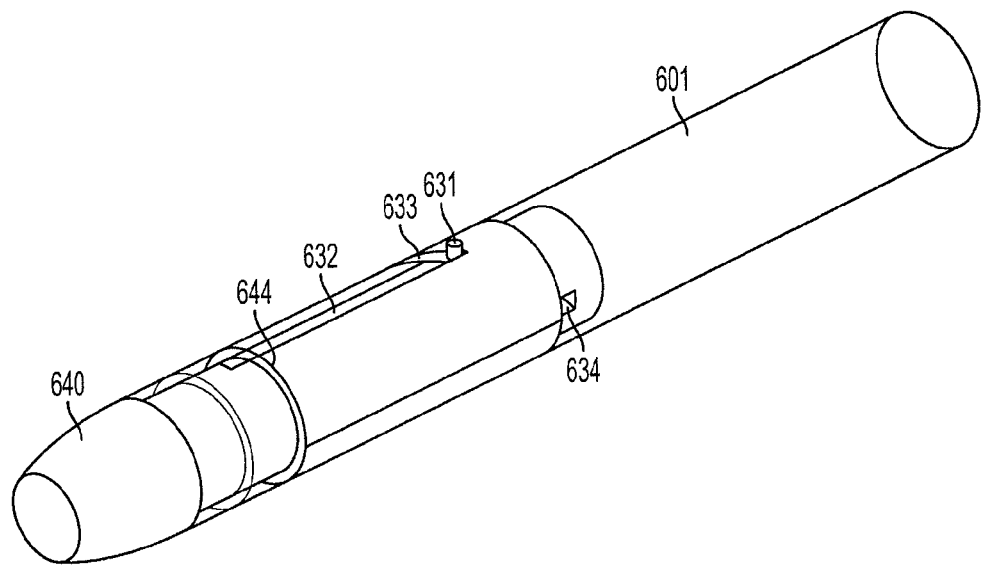
FIGS. 6A and 6B illustrate a portion of a lead extraction device comprising a slot and pin mechanism that allows for rotations of the cutting portion during operation, in accordance with some embodiments of the present invention.
Figure 6B:
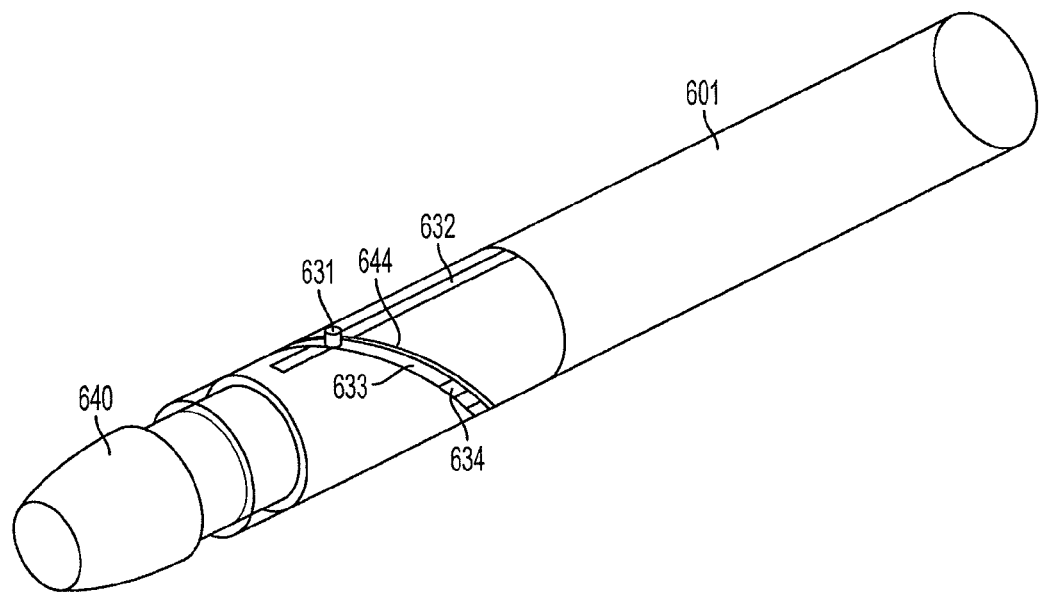

FIGS. 6A and 6B illustrate a slot and pin mechanism that allows for rotations of the cutting portion during operation. FIG. 6A illustrates a lead extraction device have a cutting portion coupled to a rotation mechanism that causes the cutting portion to rotate during advancement of the distal end of the device, in accordance with some embodiments. In FIGS. 6A and 6B, components involved in rotation are illustrated while other components of the device may be omitted in the drawing, though discussed in the description. The portion of the device includes a relatively rigid tube 601, a cutting portion 640 and a rotation component including a member 634, member 644, pin 631, axial slot 632 and diagonal slot 633.

Member 634 is coupled to the distal portion of the device and is forced forward when the device is elongated (e.g., upon inflation of one or more elongation balloons) and pin 631 is attached to member 634. Member 644 is coupled to the cutting portion and includes diagonal slot 633. As member 634 is advanced forward, the pin presses against the diagonal slot causing member 644 to rotate and advance, thus causing the cutting portion to simultaneously rotate and advance to cut incident tissue during the elongation phase of the lead extraction device. The pin and slot mechanism may be implemented in other ways, as the aspects of the invention are not limited in this respect.

Figure 7A:
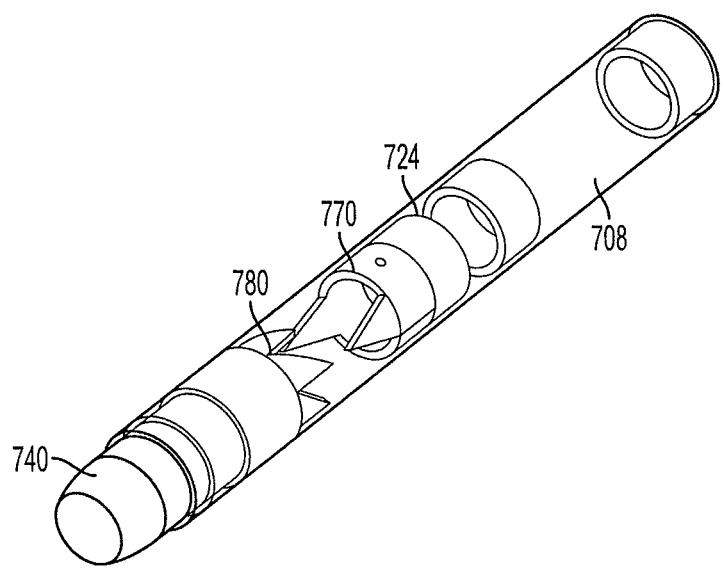
FIGS. 7A and 7B illustrate a portion of a lead extraction device having a cutting portion coupled to a rotation mechanism, in accordance with some embodiments of the present invention.
Figure 7B:
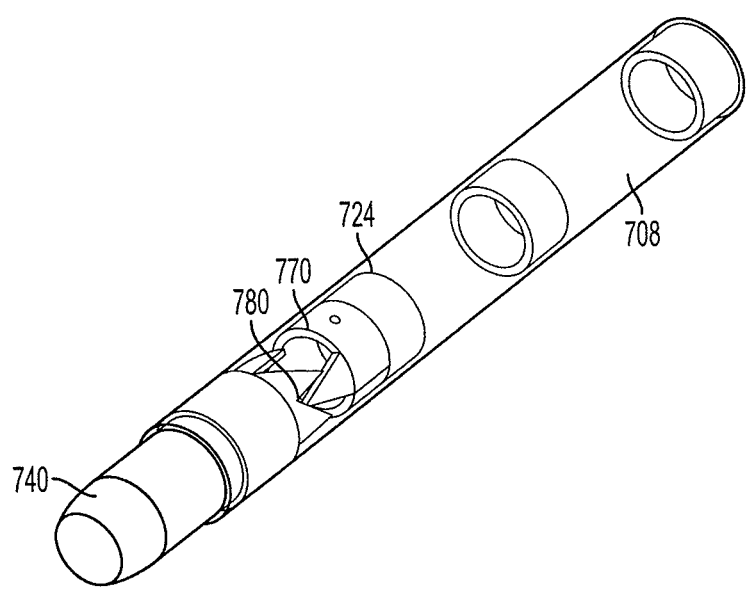

FIGS. 7A and 7B illustrate a lead extraction device having a cutting portion coupled to a rotation mechanism, in accordance with some embodiments of the present invention. The premise behind the operation of the rotation mechanism in FIG. 7 involves the interlocking of reciprocal components, for example, interlocking teeth, prongs or other cooperating structures that can be engaged. In FIG. 7, components involved in rotating the device are illustrated while other components may be omitted. The lead extraction device includes a relatively rigid tube 708, a portion of which may form the outer diameter of a proximal anchoring balloon.

A rotation component is comprised of two cooperating rotating members 770 and 780, each having reciprocal teeth that correspond to one another and engage when brought together. Member 724 moves with the distal portion of the device and is attached to one side of member 770. Accordingly, when member 724 is forced forward (e.g., by inflation of an elongation balloon), member 770 is also moved forward to engage with member 780 as illustrated in FIG. 7B. Member 780 is in turn coupled to the cutting portion 740. Once members 770 and 780 engage, the cutting portion will rotate as member 770 is force forward and rotates do the elongation operation of the device. When the elongation component contracts, the members 770 and 780 disengage and return to the position illustrated in FIG. 7A. Thus, the cutting portion is rotated during the elongation stage of the operation cycle only.

Figure 8:
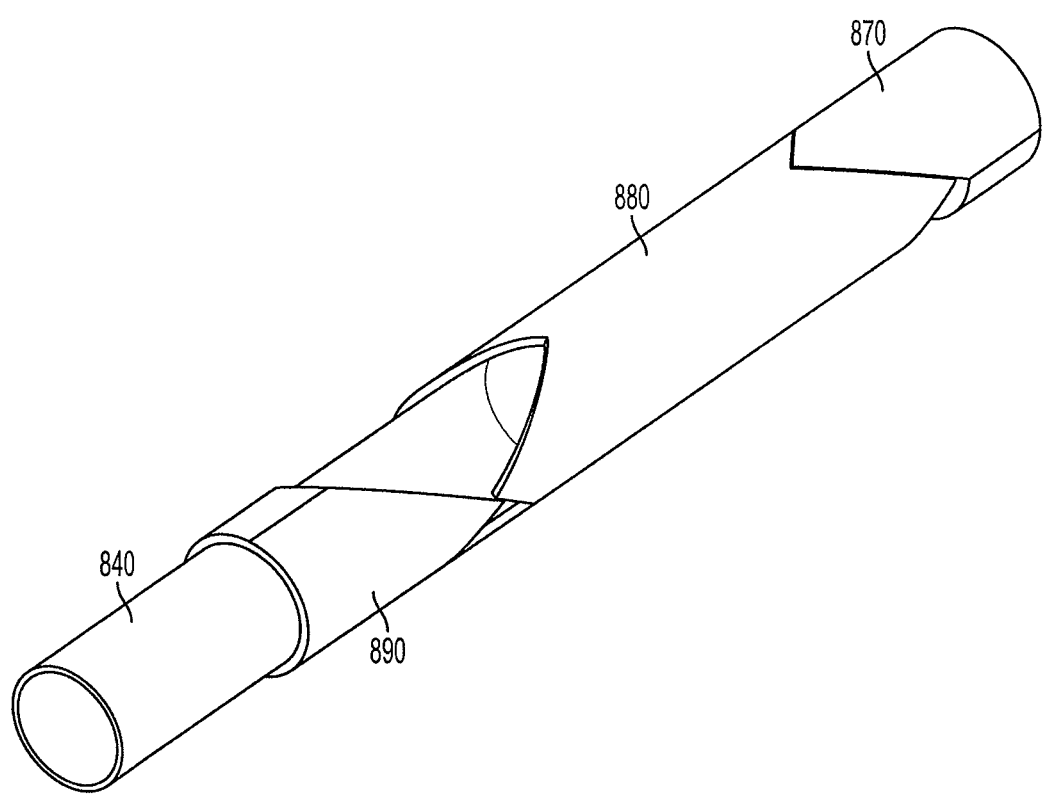
FIG. 8 illustrates the front portion of a lead extraction device having a cutting portion coupled to a rotation component, in accordance with some embodiments of the present invention.

FIG. 8 illustrates the front portion of a lead extraction device having a cutting portion coupled to a rotation component, in accordance with some embodiments of the present invention. As discussed above, components effecting a rotation of the cutting portion are illustrated while other components may be omitted. The lead extraction device in FIG. 8 is designed with a rotation component capable of rotating the cutting portion both during elongation (e.g., advancement of the distal portion) and during contraction (e.g., advancement of the proximal portion). The rotation component includes three rotation members 870, 880 and 890. Rotation members 870 and 880 may be similar in principle and operation to the coopering rotating members 770 and 780 described above in connection with FIGS. 7A and 7B, in that when rotating member 870 is forced forward and rotates, it rotates the cutting portion 840 when it engages with rotating member 880 to effect a forward advancement and rotation of the cutting portion during forward advancement of the distal portion (e.g., during an elongation phase).

In addition, rotating member 880 includes teeth structures to engage with both the rotating member 870 and rotating member 890, the latter of which effects rotation of the cutting portion during the advancement of the proximal portion of the device (e.g., during a contracting phase). Rotating member 890 may be slid over the cutting portion and forced to move in the same direction as rotating member 870. When the expansion portion of the device is elongated, rotating member 870, and thus rotating member 890, are forced towards the distal end of the device.

As discussed above, rotating member 870 engages rotating member 880 to advance and rotate the cutting portion as the expansion portion is elongated. When the expansion portion is contracted, the rotating member 870 moves back towards the proximal end, forcing rotating member 890 in the same direction. Since rotating member 880 remains static in the absence of forces from the other rotating members, rotating member 890 engages with and rotates rotating member 880 as it moves towards the proximal end. The rotation of rotating member 880 causes the cutting portion to rotate both in the elongation and contraction stages (e.g., both when the distal portion advances along the lead and when the proximal portion advances along the lead).

Figure 9:
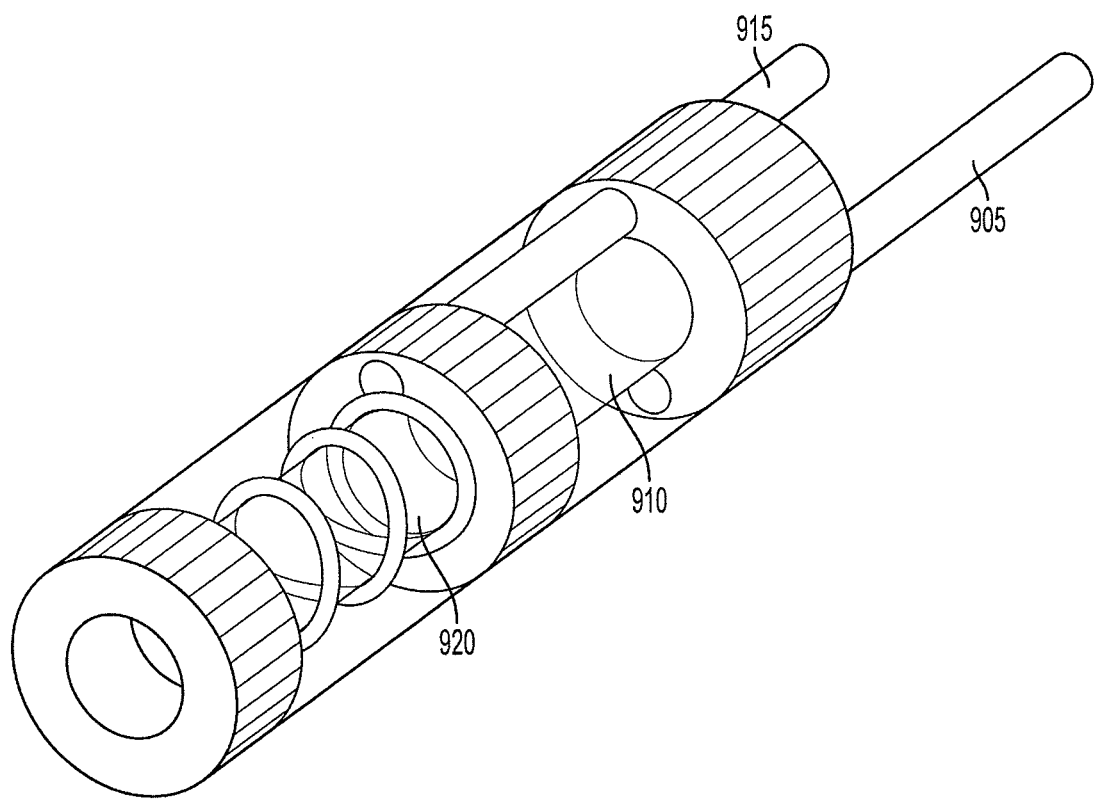
FIG. 9 illustrates a portion of a lead extraction device having inflation tubes to inflate the anchoring and expansion components, in accordance with some embodiments of the present invention.

Some aspects of the invention incorporate the underlying concept of utilizing fluid pressure changes to effect anchoring, advancing and/or cutting. According to some embodiments, fluid pressure changes cause balloons to either inflate or deflate. There are numerous ways in which the balloons can be inflated/deflated to affect anchoring, advancing and/or cutting by a lead extraction device. FIG. 9 illustrates inflating balloons via tubes, in accordance with some embodiments of the present invention. In FIG. 9, a tube 905 is coupled to proximal anchoring balloon 910 such that fluid may be forced into the proximal anchoring balloon to inflate the balloon to grip the lead. Similarly, tube 915 is coupled to elongation balloon 920 such that fluid may be forced into the balloon to elongate the balloon and stretch the spring mechanism.

In embodiments including a distal anchoring balloon, a third tube may be implemented to inflate the distal anchoring balloon in the same manner. The tubes may be of any type capable of providing fluid to the respective balloons (e.g., air, liquid or a solid such as foam). For example, the tube may have an accordion shape and/or be capable of being stretched. While the cross-section of the inflation tubes are shown as circular, the cross-section may be of any shape (e.g., elliptical), as the aspects of the invention are not limited in this respect. Alternatively, inflation may be achieved by annular tubes concentrically arranged about each of the respective components being inflated, as discussed in further detail below.

The inflation tubes may be coupled to a respective pump mechanism that allows fluid to be pumped into the device (e.g., into the respective balloon). For example, the pump mechanism may be a syringe with a spring and by pressing the syringe handle or plunger forces air/fluid into the balloons. In some embodiments, the fluid is a liquid (e.g., water, saline or some other desired solution), thus utilizing hydraulics to operate the lead extraction device. In some embodiments, the fluid is a gas (e.g., compressed air or some other gas such as an inactive or inert gas), thus utilizing pneumatics to operate the lead extraction device. In some embodiments, a combination of hydraulic and pneumatic techniques may be used to operate the lead extraction device, as the aspects of the invention are not limited in this respect.

According to some embodiments, the pump mechanism may be a squeeze pump that can be manually squeezed to fluid into the balloons (e.g., similar to squeeze balls commonly used to inflate blood pressure arm bands). The squeeze pump may include a release valve to release the pressure for deflation. Any of the various suitable pump mechanisms may be connected to a motor to inflate the respective balloons. For example, the pump mechanism may be part of a compressor unit capable of producing forced fluid. As an alternative to the embodiments discussed above in which fluid is delivered to the balloons via one or more inflation tubes, fluid may be delivered to the device via one or more annular tubes provided concentrically around the balloons. It should be appreciated that the balloons may be inflated/deflated by any other suitable means, as the aspects of the invention are not limited to any particular method by which balloons are inflated/deflated.

Figure 10:
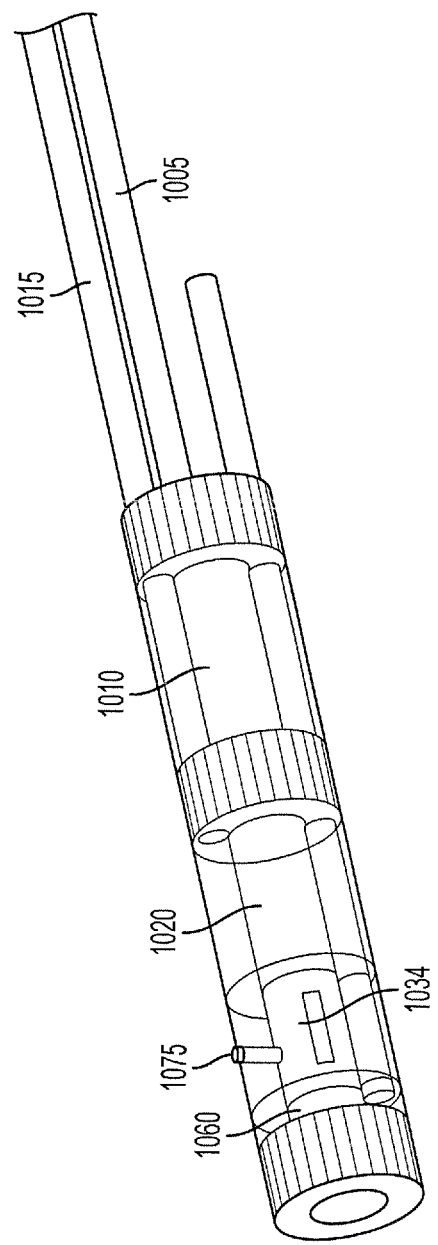
FIG. 10 illustrates a portion of a lead extraction device capable of operating without the use of a spring, in accordance with some embodiments of the present invention.

FIG. 10 illustrates a portion of a lead extraction device capable of operating without the use of a spring, in accordance with some embodiments of the present invention. The advancement of the lead extraction device in FIG. 10 may be powered by a mechanism capable of achieving sufficient forces both when inflating and deflating an elongation balloon. As with the lead extraction device described in connection with FIG. 9, balloons may be inflated and/or deflated via tubes. In particular, a proximal anchoring balloon 1010 is inflated and/or deflated via inflation tube 1005 and elongation balloon 1020 is inflated and/or deflated via inflation tube 1015. The proximal anchoring balloon and elongation balloon may operate in a manner similar to any of the mechanisms described herein. Elongation balloon 1020 pushes part 1034 of the distal portion forward and rotates (via the rotation mechanism 1075) the knife to advance the distal portion of the device forward.

Instead of having the tension in a stretched spring mechanism pull the proximal portion of the device towards the distal portion, a contracting balloon 1060 may be provided to perform substantially the same function. The energy stored in a stretched spring is replaced by energy stored in an inflated contracting balloon 1060. That is, after elongation and while elongation balloon 1020 is still inflated, the contracting balloon 1060 may be inflated to resist the distal portion and the proximal portion from coming together (e.g., similar to the resistance proffered by a stretched spring). The elongation balloon and the distal anchoring balloon may be deflated. The subsequent deflating of the contracting balloon releases the resistance and pulls the proximal portion towards the distal portion to complete the advancement of the device. This process may be repeated to advance the device along the lead. It should be appreciated that any of the cutting portions and/or rotation components discussed above can be incorporated into the springless embodiment described above in connection with FIG. 10, as the aspects of the invention are not limited for use with any particular combination of components.

As discussed above, some conventional lead extraction devices require the physician/surgeon to fully operate the device manually. This process may include manually securing one end of the lead (e.g., the portion protruding from the body and/or the portion that has been already extracted) while manually forcing the device forward to cut any connected tissue (e.g., by forcing forward a sheath having a knife on the distal end to engage with tissue interfering with the removal of the lead). This process can be very awkward for the surgeon and may be prone to error. To facilitate simpler lead extraction, various concepts described herein may be used alone or in different combinations to provide improvements to the fully manual lead extraction device. Several examples of lead extraction devices using anchoring concepts are described in further detail below.

Figure 11A:
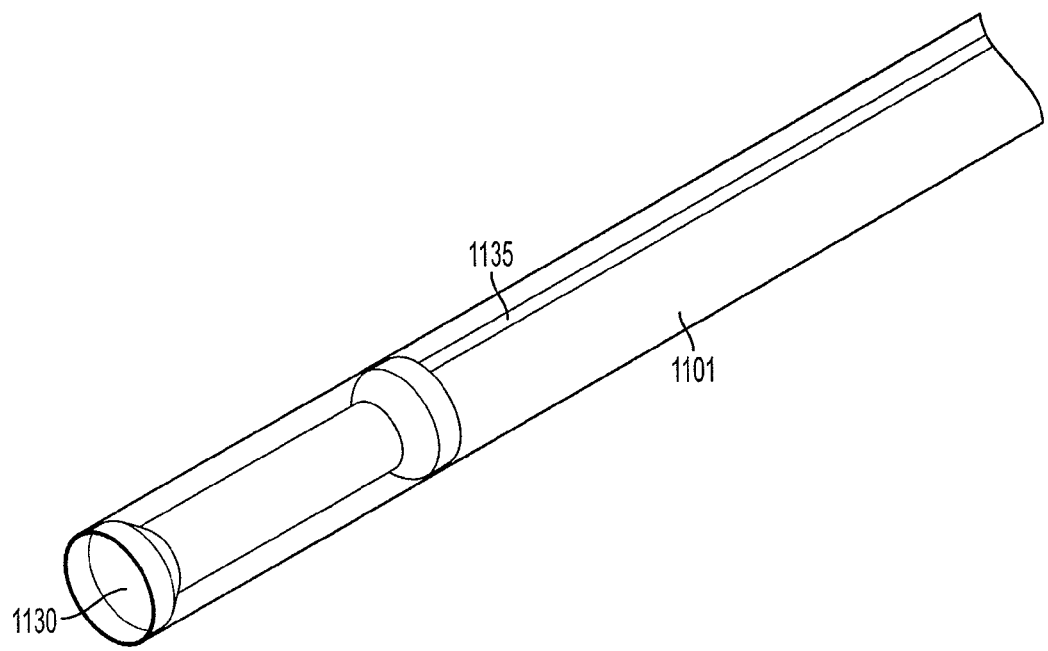
FIG. 11A illustrates a portion of a lead extraction device that uses internal anchoring to assist in lead extraction, in accordance with some embodiments of the invention.
Figure 11B:
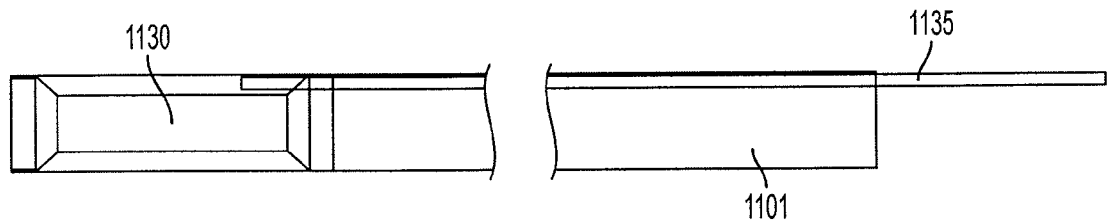
FIG. 11B illustrates a cross-section of the portion of the lead extraction device illustrated in FIG. 11A.

FIG. 11A illustrates a portion of a lead extraction device that uses internal anchoring to assist in lead extraction, in accordance with some embodiments of the invention. FIG. 11B illustrates a cross-section of the portion of the lead extraction device illustrated in FIG. 11A. According to some embodiments, an anchoring balloon 1130 is provided on a distal end of a lead extraction device. As discussed above, some conventional techniques for lead extraction involve threading a sheath having a distal cutting portion over the lead and manually forcing the sheath against obstructing tissue and/or twisting the sheath to facilitate cutting of the surrounding tissue. One or more anchoring balloons added to the distal end of such a device may facilitate separating the lead from the surrounding tissue.

In FIG. 11A, a portion of a device is illustrated having a sheath 1101. Sheath 1101 may be a conventional sheath or any type of sheath capable of being threaded over the lead. Preferably, the sheath has a relatively low rigidity for bending, but relatively high rigidity with respect to buckling and twisting. However, any suitable sheath may be used, as the aspect of the invention are not limited for use with any particular type of sheath or outer shell/body. The sheath may include a cutting portion on the distal end or may be provided without a cutting portion. One or more anchoring balloons may be provided at the distal end of the sheath. For example, an anchoring balloon 1130 of the type discussed herein may be provided such that the sheath can be anchored to and released from the lead as desired.

To operate the device, a surgeon may thread the sheath over the lead and push the device until it reaches attached tissue. The surgeon may then inflate anchoring balloon 1130 via inflation tube 1135 to anchor the device to the lead. With the device anchored proximate the attached tissue, the surgeon may pull on the device to release the lead from the attached tissue. The surgeon may also effect a twisting motion to assist in releasing the lead from the surrounding tissue. It should be appreciated that the surgeon may grip, pull and/or twist the device manually or may use other devices to assist and facilitate this motion, as the aspects of the invention are not limited in this respect. It should be appreciated that such a device may also be used in conjunction with an internal wire device that threads through the lumen of the lead and anchors to the internal lead wire coil, as discussed in the background section. For example, an anchored wire guide device may be pulled while the device is being pushed forward to the tissue and/or during the interval when the surgeon pulls/twists the anchored lead extraction device.

According to other embodiments, one or more proximal anchoring balloons may be used to facilitate extraction of a lead from a body. For example, the balloon illustrated in FIGS. 11A and 11B may be provided on the proximal side of the lead extraction device to assist in anchoring the device as a surgeon forces a connected distal portion forward along the lead. For example, the lead extraction device may have a distal portion that can be advanced independently of the proximal portion, such as a device that has an inner and an outer sheath, the outer sheath having a cutting portion that a surgeon can manually push forward to separate tissue from the lead. By providing one or more proximal anchoring balloons, the surgeon can position the device as desired and anchor the lead extraction device so that the surgeon does not have to both manually anchor the device and force forward the distal portion. Instead, the surgeon can focus on cutting the tissue at the distal end without having to worry about the proximal end of the device moving relative to the lead. This may result in freeing up one of the surgeons hand and decreasing the difficulty of the procedure.

Figure 12A:
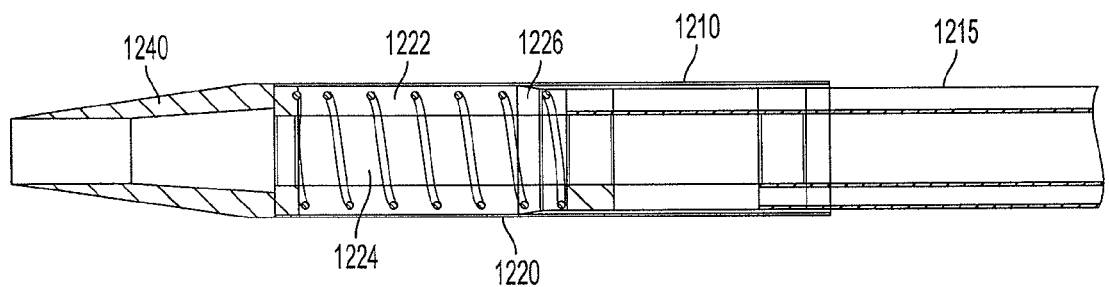
FIGS. 12A and 12B illustrate a lead extraction device having an extension portion formed from a relatively rigid outer tube and a flexible internal elongation tube, in accordance with some embodiments of the present invention.
Figure 12B:
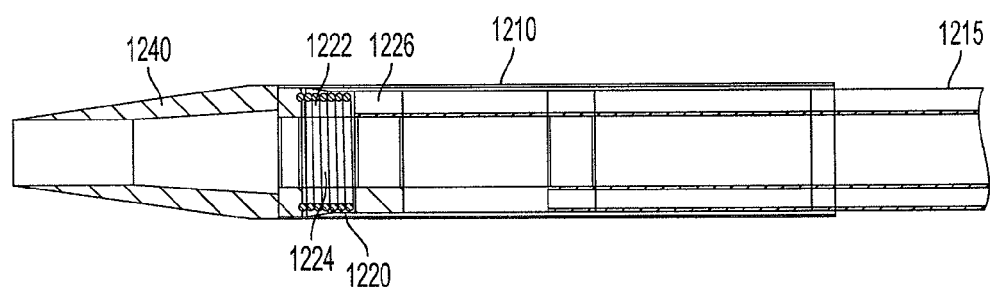

Various concepts related to anchoring, elongating and/or cutting may be improved using supplemental technology. FIGS. 12A and 12B illustrate a lead extraction device having an extension portion formed from a relatively rigid outer tube and a flexible internal elongation tube. The relatively rigid outer tube may allow increased pressure upon inflation, thus increasing the force with which the cutting portion can be advanced/rotated along the lead, thereby improving the cutting ability of the device. For example, the lead extraction device illustrated in FIGS. 12A and 12B may include a cutting portion 1240, an expansion portion 1220 and a proximal portion 1210. The proximal portion 1210 may include one or more anchoring components of any type or combination of types described herein. Similarly, cutting portion may include any type of knife and may be provided with or without one or more rotating components described herein.

The expansion portion may be improved by providing both an outer tube 1222 that is relatively rigid (e.g., a steel or plastic tube) and an inner flexible elongation tube 1224. In addition, a seal 1226 may be provided between the cavity enclosing the expansion portion and the cavity enclosing the proximal anchoring component to prevent leakage from the elongation cavity to the anchoring cavity even under relatively high pressure. The seal may be of a conical shape and made of a relatively soft material such that when the inner elongation balloon is inflated, the fluid pushes the seal to against the outer tube, preventing leakage into the anchoring cavity (e.g., possible leakage in and around the inflation tube 1215). In addition, the seal may be arranged to prevent leakage external to the device. For example, when the expansion component elongates, the portion of component 1220 that slides over component 1210 is extended and a gap may form between the two components. The seal may be arranged to prevent fluid leakage outside the device via the gap under such circumstances.

The rigid outer tube prevents expansion of the elongation tube outward such that inflation pressure provides increased force in the longitudinal direction. The increased pressure that can be used to inflate the elongation balloon (e.g., due to the outer rigid tube and/or the seal) allows the expansion portion to advance/rotate the cutting portion with greater force, improving the cutting capabilities of the device. Other sealing mechanisms can be used to increase the pressure capacity of the device, as the aspects of the invention are not limited in this respect.

Figure 13:
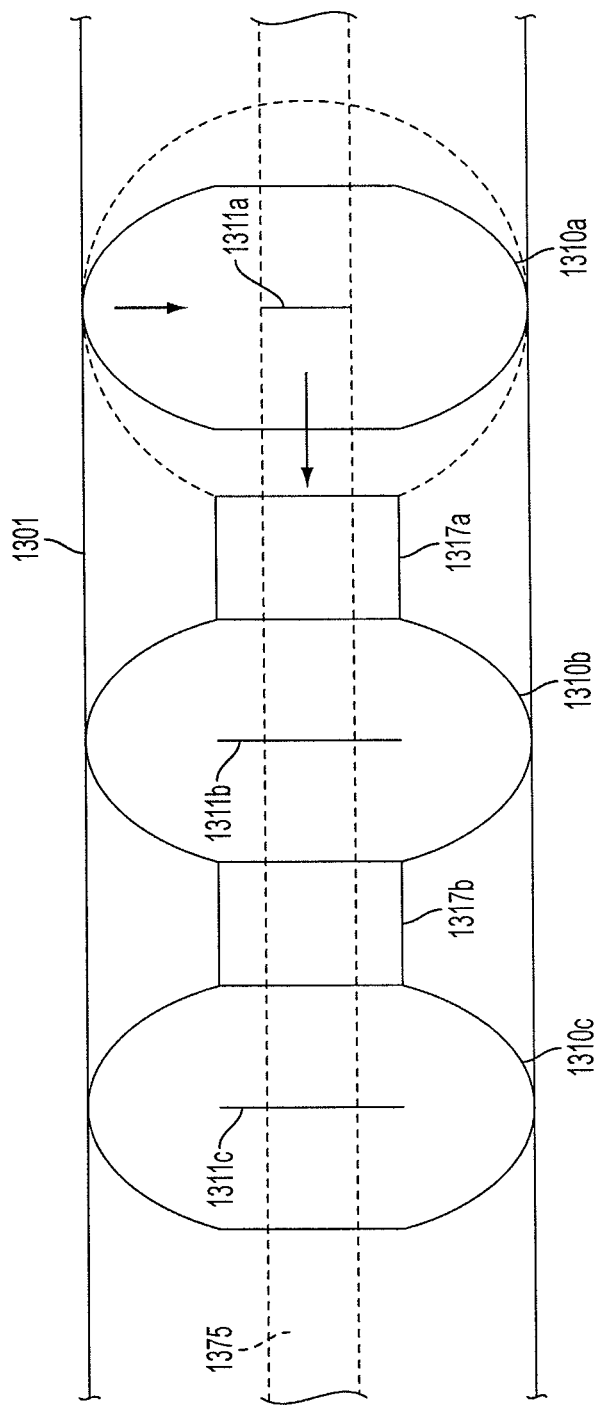
FIG. 13 is a schematic representation illustrating the principle of using a chain of balloons that each operate as both anchoring and elongation balloons, in accordance with some embodiments of the present invention.

Some aspects of the invention include using fluid pressure changes to anchor and advance/rotate a lead extraction device. For example, some embodiments include one or more anchoring balloons (e.g., proximal and/or distal anchoring balloons) and one or more elongation balloons. Applicant has appreciated that fluid pressure changes can be used to both anchor and advance/rotate a lead extraction using balloons that perform both anchoring and forward motion functions. FIG. 13 is a schematic representation illustrating the principle of using a chain of balloons that each operate as both anchoring and elongation balloons. FIG. 13 illustrates a portion of a lead extraction device having an outer tube 1301 formed from a relatively rigid material that substantially prevents balloons from inflating outwards.

The portion of the device also includes a chain of three balloons 1310a-1310c, with balloon 1310a on the proximal side of the chain and balloon 1310c on the distal side of the chain. The balloons may be toroidal in shape or any shape having a center hole through which lead 1375 may be threaded. Balloons 1310 are connected via a connector 1317 that may include a relatively short length of pipe/tube and/or a valve that prevents fluid from flowing from one balloon to another until a desired pressure differential between the balloons is achieved. The balloons are illustrated in solid lines in the deflated state. The dotted line denotes the result of inflating balloon 1310a.

As shown, the inside diameters 1311 of the deflated balloons (e.g., balloons 1310b and 1310c) are wider than the diameter of the lead so that the balloons can move relative to the lead. When balloon 1310a is inflated (e.g., via an inflation tube), the balloon expands in the two directions indicated by the arrows. Specifically, the balloon expands such that the center hole constricts and grips the lead (as shown by the reduced inner diameter 1311a of balloon 1310a) and the balloon expands along the lead as indicated by the dotted lines. The outer tube prevents the balloon from expanding outwards. The expansion of balloon 1310a along the lead forces the adjacent balloon 1310b to advance along the lead. Fluid may be continually forced into balloon 1310a. When the pressure differential between balloon 1310a and balloon 1310b reaches a threshold value determined by the pipe and/or valve, fluid is forced into balloon 1310b and the balloon begins to inflate.

In a manner similar to balloon 1310a, balloon 1310b begins to inflate to both anchor the balloon to the lead and force adjacent balloon 1310c to advance along the lead. Because balloon 1310a is anchored to the lead, the expansion of balloon 1310b does not effect the location of balloon 1310a with respect to the lead. When the pressure differential between balloons 1310b and 1310c reaches a threshold, balloon 1310c begins to inflate. When all three balloons are inflated, each balloon is anchored to the lead and the distal end of the chain has been advanced along the lead (e.g., by the sum of the incremental advancements of each balloon in the chain). It should be appreciated that the last balloon on the distal end of the chain can be coupled to a cutting portion and/or rotation component such that the expansion of the chain forces the cutting portion forward and/or rotates the cutting portion to separate incident tissue.

To advance the proximal end of the chain, the balloons are iteratively deflated from the proximal end to the distal end in a similar manner. In particular, balloon 1310a may first be deflated, releasing the lead as the inner diameter returns to its deflated dimensions. Because balloon 1310b is still anchored to the lead, the connection between balloons 1310a and 1310b causes balloon 1310a to be drawn towards balloon 1310b to advance the balloon along the lead. When the pressure differential between balloons 1310b and 1310a reaches a threshold value, balloon 1310b begins to deflate, releasing the balloons hold on the lead. Because balloon 1310c remains anchored, balloons 1310b and 1310a are drawn towards balloon 1310c due to the connection and are advanced along the lead. When the pressure differential between balloons 1310c and 1310b reaches a threshold value, balloon 1310c begins to deflate, releasing the balloons hold on the lead. Subsequently, all balloons are deflated and return to the initial state but the chain has been advanced along the lead and the cutting portion has been forced forward and/or rotated. It should be appreciated that FIG. 13 is schematic to illustrate the principle and relative dimensions may not be accurate as certain components are enlarged to better illustrate the underlying concepts.

Any number of balloons may be used to form the chain adapted to both anchor and advance a lead extraction device along the lead, as the aspects of the invention are not limited for use with any particular number of balloons. Additionally, the linking component between the balloons may be any type of component that connects the balloons and allows fluid under pressure to pass between the balloons (e.g., that prevents fluid exchange until a desired pressure differential between adjacent balloons is reached and/or exceeded). The balloons in the chain can be formed from round torus shapes, cylindrical shapes or any other suitable shape that performs anchoring and advancement during an inflation/deflation cycle, as the aspects of the invention are not limited for use with balloons of any particular shape.

As discussed above, typical heart leads cover the inner wire (or wire coil) with a dielectric material. This material is often made from silicone or a polyurethane material. Materials used for constructing balloons may also be made from the same or similar materials. Accordingly, a problem may arise that when a balloon is in the deflated state, while not gripping the lead, the inner circumference may rest against and/or contact the lead. As a result, some amount of friction remains between the inner circumference of the balloon and the lead. Depending on the extent of this friction, proper advancement of the balloons may be partially or entirely impeded, frustrating advancement of the device. Rings inserted within the inner circumference of the balloon that have some spring resistance outward to force the inner circumference of the balloon away from the lead may be provided to prevent the inner circumferences of the balloon from providing drag on the lead when deflated, as discussed in further detail below.

Figure 14A:
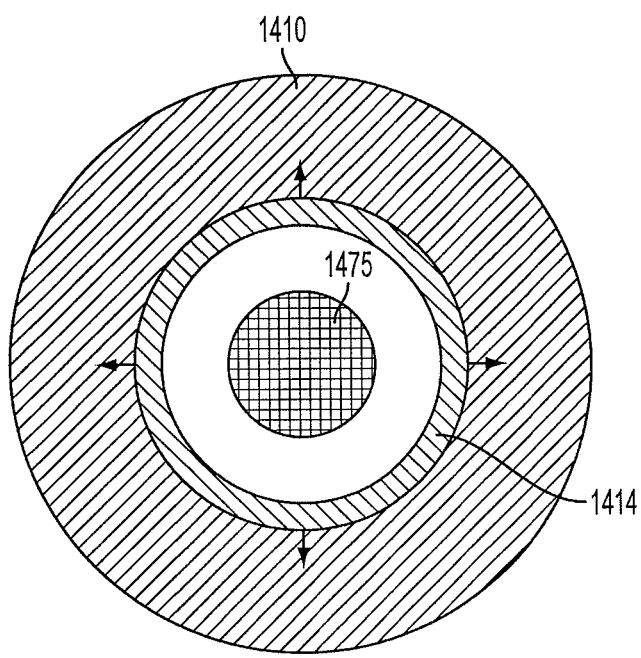
FIG. 14 illustrates a cross-section of a balloon having a ring 1414 affixed to the inner circumference of balloon 1410, in accordance with some embodiments of the present invention.

FIG. 14 illustrates a cross-section of a balloon having a ring 1414 affixed to the inner circumference of balloon 1410. Ring 1414 may be formed from an elastic material that in the absence of other greater forces, returns to a resting state wherein the diameter of the ring is as shown in FIG. 14A. However, the ring may be collapsible when an outside force is applied that is greater than the ring's natural tendency to conform to the shape illustrated in FIG. 14A. Thus, in the deflated state, the natural tendency of the ring to return to its maximum diameter forces the balloon 1410 away from the lead such that the balloon has little or no contact with the lead, allowing the balloon to move relative to the lead with relative freedom.

Figure 14B:
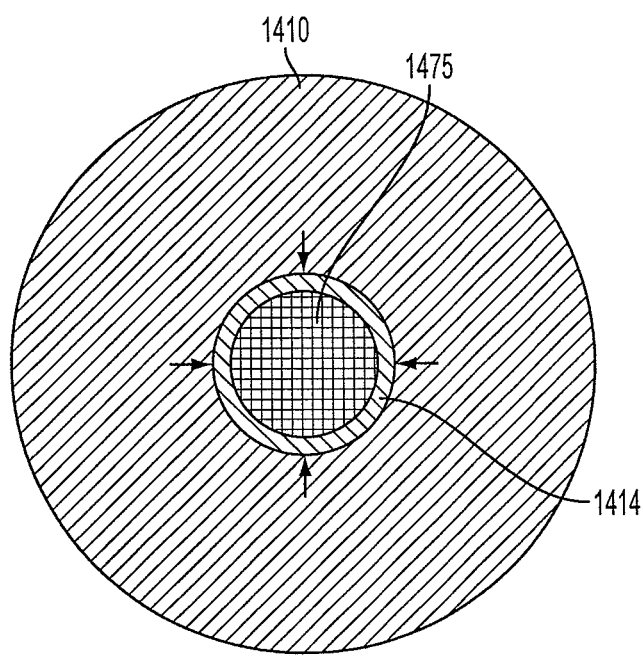

When the balloon is inflated, the force of the constricting inner circumference of the balloon becomes greater than the tendency of the ring to return to its maximum diameter. Thus, as the balloon inflates, the diameter of the ring collapses and grips the lead to anchor the balloon to the lead as illustrated in FIG. 14B. Application of the ring, therefore, may improve the operation of the balloon in the deflated state. It should be appreciated that ring 1414 may be formed from any suitable material that tends to a maximum diameter but whose diameter can be collapsed upon application of the force of an inflating balloon, as the aspects of the invention are not limited for use with rings of any particular material. Alternatively, stents may be used in place of the rings. For example, a mesh stent may be disposed proximate the inner wall of the balloon such that when the balloon is deflated, the stent forces the balloon away from the lead. Other methods of forcing the balloon away from the lead when deflated may also be used, as the aspects of the invention are not limited in this respect.

The principle of providing a balloon that provides both anchoring and advancing functions can be implemented in any number of ways. FIGS. 15A, 15B and 15C illustrate different views of a chain of balloons capable of both anchoring and advancing a lead extraction device. The chain of balloons may operate using the same or similar principle to that described in connection with FIG. 13. In the embodiments shown herein, balloons 1510 are cylindrical in shape, each connected to the adjacent balloon by a connector 1517 and inflated using inflation tube 1505. As shown in the cross-section view 15A and the magnified view in 15B, the connectors 1517 may include a valve that allows fluid to flow to adjacent balloons once a pressure differential between the adjacent balloons has been achieved. It should be appreciated that the dimensions and specific implementation illustrated in FIG. 15 is merely exemplary, and other dimensions, implementations and components may be used, as the aspects of the invention are not limited in this respect.

According to some embodiments, the principle of using the same balloons for anchoring and advancing a lead extraction device is incorporated into a single balloon. For example, a single cylindrical balloon may be used wherein the connectors are rings that are slid over the balloon and pinched to a desired diameter to create a "neck" between the segments of the balloon. Referring to FIG. 15A, according to some embodiments, component 1500 may be formed from a single cylindrical balloon. Connectors 1517 may be rings inserted over the balloon that pinch the balloon into segments 1510a-1510c. The resulting neck therefore provides the "valve" mechanism that permits fluid flow between the balloons only when a desired pressure differential has been achieved between the balloons. Other implementations that use the principle of balloons or balloon segments that both anchor and advance a lead extraction device may be used, as the aspects of the invention are not limited in this respect.

FIGS. 16A, 16B and 16C illustrate views of a lead extraction device incorporating at least some of the anchoring/advancing techniques discussed above in connections with FIGS. 13-15. In particular, component 1610 may be a chain of balloons or a chain of segments of a single balloon capable of both anchoring and advancing the lead extraction device. Any of the techniques described herein may be used to implement component 1610. In addition, component 1610 is coupled to a rotating component 1634 which is in turn coupled to cutting portion 1640. As component 1510 causes advancement, the rotation component 1634 is engaged and causes the cutting portion to rotate and advance to partially or completely separate tissue from the lead.

Rotation component 1634 may be the same or similar to any of the rotation components described herein or may be implemented in a different suitable manner, as the aspects of the invention are not limited in this respect. In addition, cutting portion 1640 may be any suitable component adapted to cut through tissue, in addition to a cutting portion adapted with heat, laser and/or RF technology to soften/ablate tissue to facilitate cutting, as the aspects of the invention are not limited in this respect. The lead extraction device in FIG. 16 is illustrated as being inflated/deflated via inflation tube 1605, however, any inflation/deflation mechanism may be used.

Figure 17A:
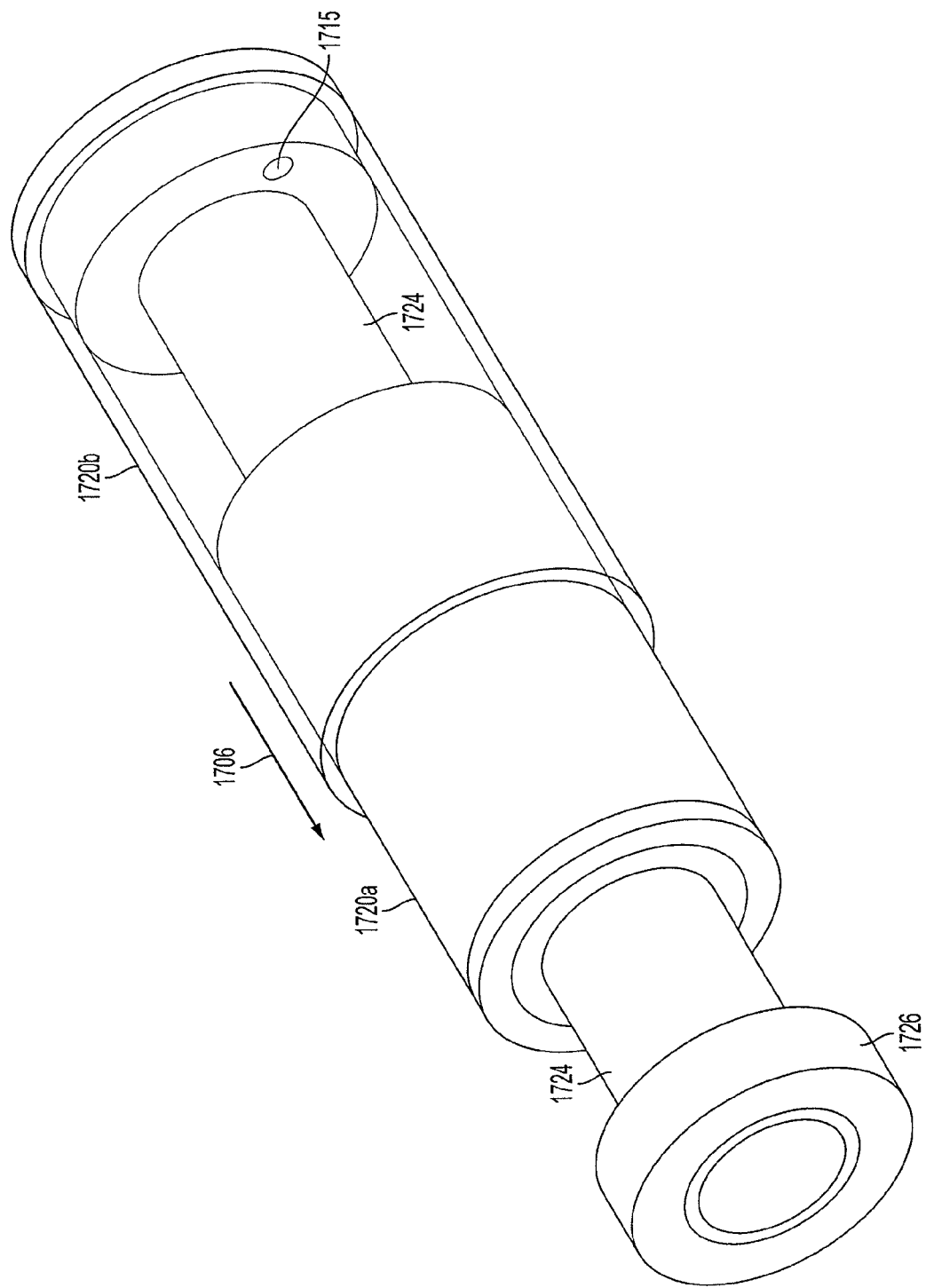
FIG. 17A illustrates a expansion portion for a lead extraction device using a piston mechanism, in accordance with some embodiments of the present invention.

FIG. 17A illustrates a expansion component for use with a lead extraction device, in accordance with some embodiments of the present invention. In FIG. 17, the expansion component uses a piston mechanism that may be either hydraulically or pneumatically operated to elongate a portion of the device to facilitate advancing the device along the lead. The expansion component may include a piston mechanism 1720, an inner tube 1724 and an end portion 1726. The piston mechanism 1720 may comprise inner part 1720a and outer part 1720b. The inner part 1720a may be moveably coupled to the outer part 1720b such that the inner part 1720a is capable of sliding into and out of outer part 1720b. Fluid pressure may be applied to the piston mechanism via hole 1715, which may in turn be connected to an inflation tube.

When fluid pressure is applied to the piston mechanism 1720, the inner part 1720a is forced out of outer part 1720b in the direction of arrow 1706. The inner part 1720a may be coupled to a cutting portion or a distal portion coupled to the cutting portion such that when the piston mechanism is inflated, the cutting portion is advanced forward. In addition, inner part 1720a may be coupled to a rotation component such that when the piston mechanism is inflated, the rotation component causes the cutting portion to rotate simultaneously with or independent from the forward motion of the cutting portion. The piston mechanism may be coupled to a spring mechanism such that when the piston mechanism is inflated, the spring mechanism is stretched. When the piston mechanism is deflated, the spring may recoil back to the repose position. The force of the spring mechanism returning to repose may force the inner part 1720a back into outer part 1720b (e.g., by pulling outer part 1720b forward).

Figure 17B:
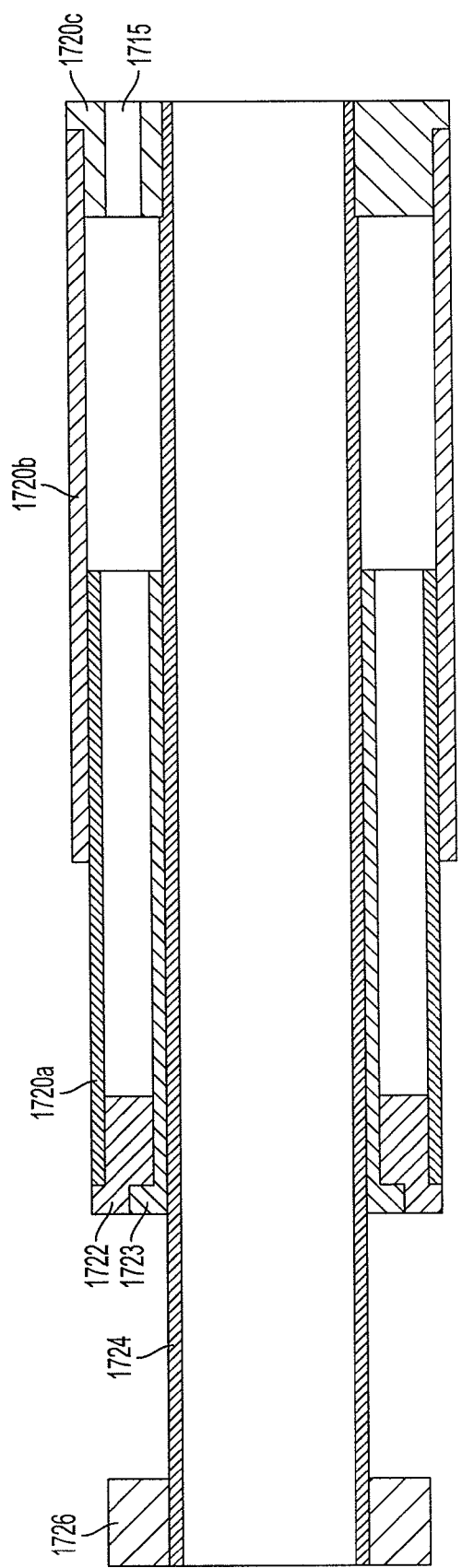
FIG. 17B illustrates a cross-sectional view of the expansion portion illustrated in FIG. 17A, in accordance with some embodiments of the present invention.

The inner tube 1724 may be a substantially rigid tube that accommodates the lead through the expansion portion. End portion 1726 may be arranged to stop the advancement of the inner part 1720a under fluid pressure. It should be appreciated that the expansion component may be used alone or with any one or combination of the other components described herein to facilitate advancement of a lead extraction device along the lead. Other piston mechanisms that elongate via fluid pressure may be used, as the aspects of the invention are not limited for use with any particular type of piston mechanism. FIG. 17B illustrates a cross-section of the expansion portion illustrated in FIG. 17A, showing parts 1722 and 1723 that allow the inner part 1720a to slide out under fluid pressure. In addition, part 1720c illustrates an end piece 1720c through which inflation tube can be inserted to inflate the piston mechanism.

Figures 1, 18A:
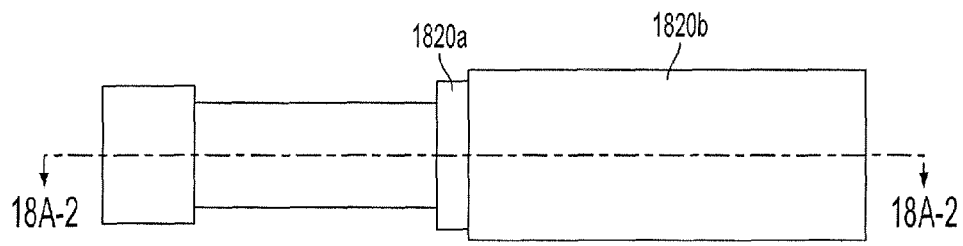
FIG. 18A illustrates a normal and cross-sectional view of an expansion portion for a lead extraction device in the deflated state, in accordance with some embodiments of the present invention.
Figures 2, 18A:
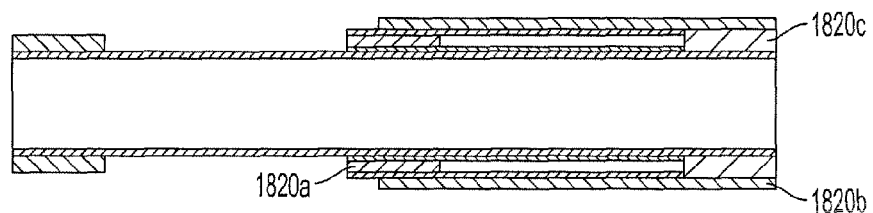
Figures 1, 18B:
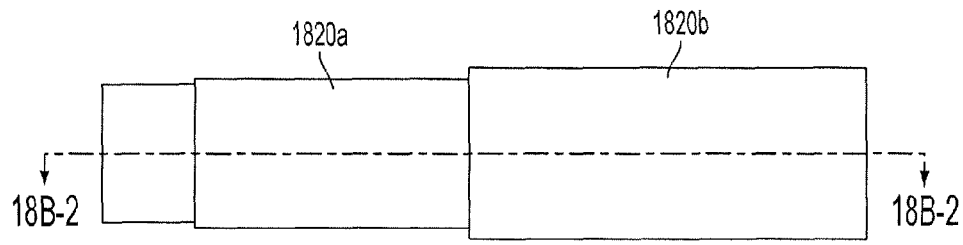
FIG. 18B illustrates a normal and cross-sectional view of an expansion portion for a lead extraction device in the inflated state, in accordance with some embodiments of the present invention.
Figures 2, 18B:
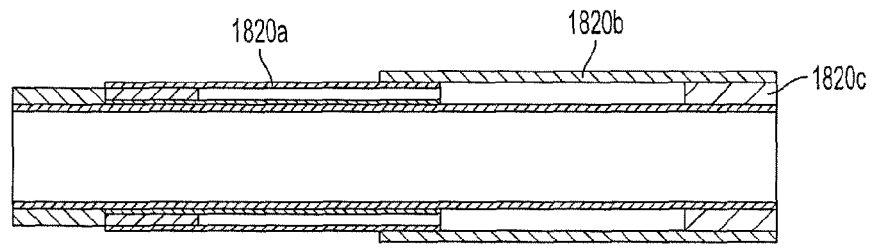

FIGS. 18A and 18B illustrate a expansion portion for a lead extraction device in a deflated state (both a normal view and a cross-section view) and in an inflated state (both a normal view and a cross-section view), respectively. The expansion portion includes a piston mechanism 1820 that may comprise an inner part 1820a, an outer part 1820b and an end piece 1820c. The piston mechanism may operate in a manner similar or different than the piston mechanism described in connection with FIGS. 17A and 17B, as long as the inner part 1820a can be extended upon application of fluid pressure. As shown in FIG. 18A, when the expansion component is in the deflated state, the inner part 1820a is substantially within outer part 1820*b*. When fluid pressure inflates the piston mechanism as shown in FIG. 18B, inner part 1820*a* is forced outwards along the lead. Other parts, components and mechanism may be included in the expansion portion, as the aspects of the invention are no limited in this respect.

The above-described embodiments of the present invention can be implemented in any of numerous ways, and the examples described herein are not limiting. In addition, various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. In particular, the various concepts relating to anchoring, advancing and cutting may be implemented in any way and be used alone or in any combination. The invention is capable of other embodiments and of being practiced or of being carried out in various ways.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A device for assisting in removing an implanted lead, the device comprising:
    a body having a proximal portion and a distal portion, the body adapted to accommodate the lead;
    at least one expansion component capable of increasing a distance between the proximal portion and the distal portion, the at least one expansion component comprising a piston mechanism having a piston arranged to slide forward and backward in an axial direction with respect to the body into and out of an outer part, wherein the piston is forced in a forward direction along the lead and outwards from the outer part when fluid pressure is applied to the piston mechanism;
    a separating component coupled to the at least one expansion component such that when fluid pressure is applied to the piston mechanism, the separating component is forced in a forward direction along the lead by the piston to assist in separating tissue from the lead;
    at least one proximal anchoring component capable of providing pressure on the lead that resists movement of at least part of the proximal portion along the lead at least in part by fluid pressure applied to the at least one proximal anchoring component to provide an anchor against which the separating component can be forced in the forward direction to assist in separating tissue from the lead, the at least one proximal anchoring component arranged proximally to the piston mechanism;
    at least one distal anchoring component capable of providing pressure on the lead that resists movement of at least part of the distal portion along the lead at least in part by fluid pressure applied to the at least one distal anchoring component to anchor at least part of the distal portion to the lead subsequent to advancing the distal portion by applying fluid pressure to the at least one expansion component, the at least one distal anchoring component located distally to the piston mechanism so that the piston mechanism is located between the at least one proximal anchoring component and the at least one distal anchoring component; and
    a spring mechanism coupled between the proximal portion and the distal portion, wherein the spring mechanism is stretched when fluid pressure is applied to the piston mechanism and contracts to advance the proximal portion when fluid pressure is released from the at least one expansion component and the at least one proximal anchoring component.

2. The device of claim 1, wherein by applying fluid pressure, in sequence, to the at least one proximal anchoring component, the at least one expansion component, and the at least one distal anchoring component at locations along the lead where the device encounters tissue adhered to the lead, the device is capable of advancing through the tissue by applying local force on the tissue.

3. The device of claim 1, wherein the piston comprises a central hole adapted to allow the piston to pass over the lead when the piston slides into or out of the outer part.

4. The device of claim 1, wherein the outer part comprises a cylindrical portion within which the piston fits and slides into and out of and into which fluid is applied to force the piston forwards and outwards from the cylindrical portion.

5. The device of claim 1, wherein the at least one distal anchoring component, when fluid pressure is applied to the at least one distal anchoring component, causes gripping contact on a full circumference of a portion of the lead.

6. The device of claim 1, wherein the at least one proximal anchoring component, when fluid pressure is applied to the at least one proximal anchoring component, causes gripping contact on a full circumference of a portion of the lead.

7. The device of claim 1, wherein the at least one distal anchoring component comprises at least one anchoring balloon that provides pressure on the lead that resists movement of the distal portion along the lead when inflated.

8. The device of claim 1, wherein the at least one proximal anchoring component includes at least one anchoring balloon that provides pressure on the lead to resist movement of the proximal portion along the lead when inflated.

9. The device of claim 1, further comprising a rotating component coupled to the separating component and the at least one expansion component, wherein when fluid pressure is applied to the at least one expansion component, force from the at least one expansion component causes the rotating component to rotate the separating component while the separating component is being forced in the forward direction along the lead to assist in separating tissue from the lead.

10. The device of claim 1, wherein by applying fluid pressure, in sequence, to the at least one proximal anchoring component, the at least one expansion component, and the at least one distal anchoring component, the device is advanced along the lead to separate tissue from the lead.

11. The device of claim 1, wherein the outer part includes a cylindrical portion, and wherein the piston comprises a cylindrical part that fits within the cylindrical portion and a hole that allows the piston to pass over the lead.

12. The device of claim 1, further comprising a first inflation tube through which fluid is applied to the at least one proximal anchoring component, a second inflation tube through which fluid is applied to the piston mechanism, and a third inflation tube through which fluid is applied to the at least one distal anchoring component so that the at least one proximal anchoring component, the piston mechanism and the at least one distal anchoring component are configured to be operated independently.

* * * * *